(12) United States Patent
Konya

(10) Patent No.: US 8,998,940 B2
(45) Date of Patent: Apr. 7, 2015

(54) LANCET GRIPPER FOR USE IN A LANCET DEVICE

(75) Inventor: Ahmet Konya, Ludwigshafen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 585 days.

(21) Appl. No.: 13/459,921

(22) Filed: Apr. 30, 2012

(65) Prior Publication Data

US 2012/0253374 A1 Oct. 4, 2012

Related U.S. Application Data

(63) Continuation of application No. PCT/EP2010/066465, filed on Oct. 29, 2010.

(30) Foreign Application Priority Data

Nov. 2, 2009 (EP) ..................................... 09174764

(51) Int. Cl.
*A61B 5/151* (2006.01)
*A61B 5/15* (2006.01)

(52) U.S. Cl.
CPC .................................... *A61B 5/1411* (2013.01)

(58) Field of Classification Search
CPC ............. A61B 5/1411; A61B 5/15146; A61B 5/15148; A61B 5/15153; A61B 5/15165; A61B 5/15169; A61B 5/15171
See application file for complete search history.

(56) References Cited

U.S. PATENT DOCUMENTS

| 6,530,892 | B1 * | 3/2003 | Kelly | 600/583 |
|---|---|---|---|---|
| 6,783,537 | B1 * | 8/2004 | Kuhr et al. | 606/182 |
| 7,211,096 | B2 * | 5/2007 | Kuhr et al | 606/182 |
| 7,959,581 | B2 | 6/2011 | Calasso et al. | |
| 8,052,926 | B2 * | 11/2011 | Joseph et al. | 422/22 |
| 8,234,767 | B2 * | 8/2012 | Roeper et al. | 29/418 |
| 8,591,436 | B2 * | 11/2013 | Roe et al. | 600/583 |
| 8,758,382 | B2 * | 6/2014 | Sacherer | 606/182 |
| 2002/0120216 | A1 * | 8/2002 | Fritz et al. | 600/583 |
| 2003/0199893 | A1 * | 10/2003 | Boecker et al. | 606/181 |
| 2003/0211619 | A1 | 11/2003 | Olson et al. | |
| 2004/0039303 | A1 * | 2/2004 | Wurster et al. | 600/584 |
| 2004/0087990 | A1 * | 5/2004 | Boecker et al. | 606/181 |

(Continued)

FOREIGN PATENT DOCUMENTS

| CA | 2 680 855 A1 | 10/2008 |
|---|---|---|
| CA | 2 700 330 A1 | 3/2009 |

(Continued)

*Primary Examiner* — Ryan Severson

(74) *Attorney, Agent, or Firm* — Bose McKinney & Evans LLP

(57) ABSTRACT

A gripper device for use in a lancet device for generating a sample of a body fluid. In the lancet device, a plurality of lancets can be provided in succession on a carrier element in an application position. The gripper device is equipped to seize one lancet at a time in the application position and carry out a piercing movement using the lancet. The gripper device includes at least one stop element, which is equipped to stop the lancet in the application position and temporarily prevent further movement of the carrier element. The gripper device further includes at least one positioning element, which is equipped to position the lancet during the piercing movement in a direction transverse to a piercing direction. The gripper device can further include at least one counter-gripper, which is equipped to cooperate with the stop element whereby the lancet can be held with a form fit.

33 Claims, 15 Drawing Sheets

(56) References Cited

U.S. PATENT DOCUMENTS

| | | | |
|---|---|---|---|
| 2004/0193072 A1* | 9/2004 | Allen | 600/583 |
| 2004/0230216 A1* | 11/2004 | Levaughn et al. | 606/181 |
| 2005/0027211 A1* | 2/2005 | Kuhr et al. | 600/583 |
| 2005/0033340 A1* | 2/2005 | Lipoma et al. | 606/181 |
| 2005/0234494 A1* | 10/2005 | Conway et al. | 606/181 |
| 2005/0245845 A1 | 11/2005 | Roe et al. | |
| 2005/0245954 A1* | 11/2005 | Roe et al. | 606/181 |
| 2006/0264996 A1* | 11/2006 | LeVaughn et al. | 606/181 |
| 2007/0038150 A1* | 2/2007 | Calasso et al. | 600/583 |
| 2008/0103415 A1* | 5/2008 | Roe et al. | 600/583 |
| 2008/0300509 A1 | 12/2008 | Hoenes et al. | |
| 2009/0010802 A1* | 1/2009 | Joseph et al. | 422/22 |
| 2010/0042130 A1* | 2/2010 | Curry et al. | 606/181 |
| 2010/0049092 A1 | 2/2010 | Konya et al. | |
| 2010/0145376 A1 | 6/2010 | Konya et al. | |
| 2010/0216246 A1 | 8/2010 | Konya et al. | |
| 2010/0222799 A1* | 9/2010 | Roeper et al. | 606/181 |
| 2010/0234869 A1* | 9/2010 | Sacherer | 606/182 |
| 2010/0292609 A1* | 11/2010 | Zimmer et al. | 600/583 |
| 2012/0041339 A1* | 2/2012 | Kuhr et al. | 600/575 |
| 2012/0253374 A1* | 10/2012 | Konya | 606/181 |
| 2012/0283539 A1* | 11/2012 | Freeman et al. | 600/365 |
| 2013/0053660 A1* | 2/2013 | Shieh | 600/309 |
| 2013/0324807 A1* | 12/2013 | Kuhr et al. | 600/309 |
| 2014/0052025 A1* | 2/2014 | Roe et al. | 600/583 |

FOREIGN PATENT DOCUMENTS

| | | |
|---|---|---|
| CN | 1456891 A | 11/2003 |
| CN | 1972632 A | 5/2007 |
| DE | 28 03 345 | 6/1979 |
| DE | 2803354 A1 | 8/1979 |
| EP | 1 360 935 A1 | 11/2003 |
| EP | 1 980 205 A1 | 10/2008 |
| EP | 1 990 001 A1 | 11/2008 |
| EP | 1 997 429 A1 | 12/2008 |
| EP | 2 039 293 A1 | 3/2009 |
| WO | WO 2005/104948 A1 | 11/2005 |
| WO | WO 2005/107596 A2 | 11/2005 |
| WO | WO 2008/125178 A1 | 10/2008 |
| WO | WO 2008/145625 A2 | 12/2008 |
| WO | WO 2009/037341 A1 | 3/2009 |

* cited by examiner

LANCET GRIPPER FOR USE IN A LANCET DEVICE

RELATED APPLICATIONS

This application is a continuation of PCT/EP2010/066465, filed Oct. 29, 2010, which claims priority to EP 09174764.2, filed Nov. 2, 2009, both of which are hereby incorporated by reference in their entireties.

BACKGROUND

The disclosed embodiments relate to a gripper device that can be used as a lancet gripper in a lancet device for generating a sample of a body fluid. The disclosed embodiments further relate to a lancet device for generating a sample of a body fluid. Gripper devices and lancet devices of this kind can be used in the field of medical diagnostics for easily and quickly generating samples of body fluid, for the purpose of subsequent analysis and/or diagnosis. For example, the lancing device can be used to generate samples of blood and/or interstitial fluid for the purpose of a qualitative and/or quantitative detection of at least one analyte in the sample, for example at least one metabolite. Without excluding further possible uses, the invention is described below principally on the basis of blood glucose analysis. However, other uses are also possible.

The examination of blood samples or of other samples of body fluids, for example interstitial fluid, permits early and reliable detection of pathological conditions and also specific and reliable monitoring of physical states. Medical diagnostics generally entail collecting a sample of blood or of interstitial fluid from the individual who is to be examined. To collect the sample, the skin of the person to be examined can be punctured, for example, at the finger pad or ear lobe, with the aid of a sterile, pointed or sharp lancet, in order to collect a few microliters or less of blood for the analysis. This method is particularly suitable for sample analysis that is carried out directly after the sample has been collected.

In the area of home monitoring, where persons without specialist medical training carry out simple analyses of blood or of interstitial fluid themselves, and particularly for diabetics taking blood samples to monitor their blood glucose concentration on a regular basis, several times a day, lancets and associated appliances are offered for sale. The appliances, which are also referred to as puncturing aids, are intended to allow samples to be taken with the least possible discomfort and in a reproducible manner.

In addition to puncturing aids in which individual lancets are used that are not connected to one another by a common carrier element, the prior art also discloses tape appliances for multiple puncturing aids in which a plurality of lancets are stored and connected via a common carrier tape. DE 28 03 354 B1, for example, describes a blood-sampling appliance with a needle which can be moved against the body surface of a patient by the application of a force, and with a suitable actuating mechanism having a ram and a trigger. Blood lancets are used as needles, the blood lancets being accommodated individually in pockets of a strip package and being introduced into the blood-sampling appliance by means of a transport mechanism acting on the strip package. The document discloses a transport mechanism in the form of a drum with driver pins, with the drum being advanced step by step in order to provide the blood lancets.

EP 1 360 935 A1 discloses a continuous strip of test elements. These are each accommodated individually in a watertight package and comprise a micro-needle with an integrated test strip sensor. A roller drive is proposed, and the strip has a multiplicity of equidistant holes which are engaged by transport pins. In this way, the strip is in each case advanced by a fixed amount.

WO 2005/104948 A1 describes a test magazine with two film tapes which are connected to each other in a sandwich formation and can be wound up. Between the film tapes, receiving compartments for test elements are kept free. Piercing units and test units are arranged separately from one another in separate receiving compartments. A tape-pulling device with two winding reels is provided and tears the two film tapes apart in order to supply the puncturing units in succession.

WO 2005/107596 A2 discloses a supply of lancets for a multi-lancet appliance. The lancets are transported on a tape and are brought in succession from a storage position to an application position by means of the tape being transported about a deflector. By means of a corresponding actuator mechanism, the tape is moved into the application position such that the lancet located in the application position performs, along with the tape, a piercing movement.

WO 2008/125178 A1 discloses a piercing system for collecting a sample of body fluid, which system comprises at least one magazine containing a lancet carrier and a plurality of lancets. The document also discloses a piercing appliance having a compartment for the magazine. The appliance has an incremental advancing mechanism in order to bring the lancets contained in the magazine successively into a piercing position. Furthermore, a pierce drive is provided with which a lancet positioned in the piercing position is accelerated for a piercing movement. By means of an incremental advancing mechanism, a roller is rotated to such an extent that a fresh lancet of the lancet carrier moves into the piercing position for a piercing procedure.

These known lancet devices, in which lancets are stored on a tape, however, cause a number of difficulties in practice and pose certain challenges. In particular, the exact positioning of the lancets in the application position is a technical challenge, particularly since tolerances may arise to some extent in the manufacture of the lancet tapes. The positioning means known from the prior art, however, are generally based on an equidistant incremental advancement of the lancet tape, in many cases supported by positioning holes on the lancet tape. These mechanisms do not adequately allow for possible tolerances in the positioning of the lancets on the lancet tapes.

Therefore, WO 2009/037341 A1 discloses a combination drive for a sampling system for collecting a liquid sample. Among other things, it proposes stopping the tape transport of a test element tape only when a corresponding mechanism detects a change of thickness of the analysis tape in an application position. For this purpose, a gripper is proposed that scans the thickness of the analysis tape. If a lancet that is to be used strikes against an intended edge of the gripper, a counteracting force is applied to the analysis tape and stops further transport of the analysis tape. The gripper thus acts as a blockade element. After the lancet has been used, the gripper can be briefly opened or otherwise freed, either automatically or manually, in order to permit further transport of the analysis tape. The gripper can be designed as a spring-loaded gripper, for example, in order to ensure that a force applied to the analysis tape is sufficient to allow the analysis tape to be stopped.

EP 1 990 001 A1 describes a piercing system with a carrier tape having a plurality of lancets. Among other things, a barrier is disclosed which blocks further transport of the carrier tape as soon as a lancet has reached a use position. A coupling head is used for this, with a gap through which the carrier tape is guided. The coupling head comprises two parts, between which the gap is formed, and which are pressed against each other by spring force, such that manufacturing tolerances can be compensated. The coupling part has an abutment surface. In the use position, the lancet strikes against the abutment surface, such that the abutment surface forms a barrier element, which prevents further transport of the lancet. After the piercing procedure has been triggered, the coupling elements can be moved against each other, such that the gap temporarily widens and the carrier tape can be transported onward.

Thus, the grippers described in WO 2009/037341 A1 and EP 1 990 001 A1 provide a releasable stop function, which detects an individual positioning of the lancets on the analysis tape. However, releasable stop functions of this kind take up quite a lot of space in practice, which is disadvantageous especially in the case of compact, transportable lancet devices or in the case of lancet devices that are integrated in an analysis appliance with additional analysis function. A further technical challenge presented by simple grippers with a stop function is that the piercing movement often takes place in a relatively uncontrolled manner, since a tensioning of the carrier tape may, for example, cause the lancets to bend in the application position, as a result of which a defined and uniform piercing movement can be compromised.

It is therefore desirable to make available a gripper device and a lancet device that at least substantially avoid the disadvantages of known gripper devices and lancet devices. In particular, it is desirable to compensate for tolerances in the positioning of the lancets on the carrier element while at the same time ensuring a high degree of integration and a small overall structure and also a uniform and reproducible piercing movement.

SUMMARY

A gripper device and a lancet device are disclosed. The gripper device can be used in a lancet device for generating a sample of a body fluid.

In one form of the gripper device and the lancet device, the lancet device includes a plurality of lancets which can be provided in succession on a carrier element in an application position. The gripper device is equipped to seize one lancet at a time in the application position and carry out a piercing movement using the lancet. The gripper device includes at least one stop element which is equipped to stop the lancet in the application position and temporarily prevent further movement of the carrier element. The gripper device also includes at least one positioning element which is equipped to position the lancet during the piercing movement in at least one direction transverse to a piercing direction. The gripper device additionally includes at least one counter-gripper, wherein the counter-gripper cooperates with the stop element such that the lancet can be held with a form fit.

Various advantageous refinements of the gripper and lancet devices can be realized singly or in combination and are described herein.

In a first embodiment, a gripper device for use in a lancet device for generating a sample of body fluid is proposed. In a second embodiment, a corresponding lancet device for generating a sample of a body fluid is proposed that includes one of the gripper devices described below. For possible embodiments of the lancet device, reference can therefore be made to the description of the gripper device, and vice versa. The lancet device can be designed as a piercing aid or can be a component part of a piercing aid. Alternatively, the lancet device can be a component part of an integrated test appliance which, in addition to a lancet function, can include further functions, for example one or more analysis functions.

The lancet device is equipped in such a way that a plurality of lancets can be provided in succession therein on a carrier element in an application position. An application position is to be understood as a position in which, by means of at least one lancet provided in this position, a piercing movement can be carried out in order to perforate part of a user's skin. For example, the lancet device for this purpose can have a corresponding actuation mechanism, which will be described by way of example and in more detail below.

A lancet is generally to be understood as an element with which a perforation of a skin part is possible in order to collect a sample of the body fluid. For example, the lancets can for this purpose have a tip and/or a cutting edge. Various types of lancets can be provided. For example, round lancets with needle elements can be used. Alternatively, or in addition, flat lancets can also be used, for example, lancets that are punched out, cut out or etched out from a metal strip or are generated in a similar way. The lancets can perform what is purely a piercing function or cutting function in order to perforate the skin part. Alternatively, the lancets can also assume additional functions, for example sampling functions such as sample collection functions. Thus, for example, the lancets can each comprise one or more capillary elements in order to transport a sample of the body fluid from the body tissue of the user to a test field. Accordingly, the lancets can be designed, for example, as microsamplers, that is to say as lancet elements with an integrated capillary element such as at least one capillary gap. Moreover, the lancets can comprise one or more test elements, for example, one or more test fields with a test chemical that changes one or more physical and/or chemical properties in the presence of the at least one analyte that is to be detected. Various embodiments are possible.

A carrier element is to be understood in principle as any element, preferably any continuous element, that connects the plurality of lancets to one another. For example, the carrier element can be designed as a carrier tape. Thus, the carrier tape can, for example, comprise one or more tape-shaped carriersn made of a plastic material and/or of a paper material. For example, the lancets can be positioned on the carrier element substantially equidistantly, that is to say apart from position tolerances. For example, the carrier element can have a longitudinal direction which, for example, can correspond to a transport direction of the carrier element. The lancets are preferably positioned relative to the carrier element in such a way that the lancet tips extend transversely with respect to the longitudinal direction of the carrier element. For example, the lancet tips may extend transversely with respect to the tape direction and may be substantially perpendicular to the tape direction. The carrier element can be flexible. Accordingly, the carrier element can, for example, be guided through a corresponding guide which may involve a suitable deflection. For example, the carrier element can be bent in the application position in such a way that the lancet tip of the lancet located in the application position is exposed in order to carry out a piercing movement.

The carrier element can be designed, for example, as a carrier tape and may be received by means of one or more reels in the lancet device. For example, the lancet device can have a supply reel for providing unused lancets and a take-up reel for winding up sections of the carrier element with already used lancets. The supply reel and the take-up reel can, for example, be permanently integrated in the lancet device. Alternatively, they can be exchangeable, for example by being part of an exchangeable tape cassette that can be inserted into the lancet device. The lancet device can have a transport mechanism for transporting the carrier element onward, for example, a corresponding drive for driving the take-up reel in order to spool the carrier element off from the supply reel. It will be noted that, as an alternative to a design of the carrier element as a carrier tape, other designs are in principle also conceivable. For example, designs with a link chain, or another kind of carrier element by which the plurality of lancets are connected to one another can be used. However, a carrier tape is preferred such that the carrier tape together with the lancets form a lancet tape.

In addition to the lancets, the carrier element can also include or receive one or more further elements. For example, the carrier element can include one or more test elements, and/or one or more test elements can be connected to the carrier tape. For example, each lancet can be assigned a respective test element, the latter being integrated in the lancet or spaced apart from the lancet on the carrier element which may be a carrier tape. As has been mentioned above, the test elements can, for example, each include one or more test fields with a test chemical for the qualitative and/or quantitative detection of the at least one analyte. However, a design purely as a lancet tape, with lancets preferably arranged equidistantly, is also possible in principle. Alternatively or in addition, a non-equidistant arrangement is also possible. After the piercing procedure, the lancets preferably remain on the carrier element, such that they can be disposed of with the carrier element. As has been described above, the carrier element can, for example, be wound up onto a take-up reel. The carrier element and the lancets can be fixedly connected to each other, such that, during the piercing procedure, the carrier element is also moved, at least in the application position.

Except for the gripper device described in detail below, lancet devices of this kind can in principle correspond substantially to the lancet devices known from the prior art. In particular, the lancet device, except for the gripper device described below, can be designed wholly or partially like the sampling system described in WO 2009/037341 A1 and/or can comprise such a sampling system. Accordingly, the sampling system can comprise a coupling element and a drive unit. Reference can be made to WO 2009/037341 A1 for further possible details and counterpart publication U.S. Pat. Pub. No. 2010/0216246 is hereby incorporated herein by reference. However, other designs of the lancet device are also possible in principle.

The gripper device is designed for use in the described lancet device. The gripper device is equipped to seize one lancet at a time in the application position and carry out a piercing movement using the lancet. A piercing movement is to be understood as a movement directed toward a skin surface of a user, advantageously followed by a return movement. For example, this piercing movement can be directed perpendicularly with respect to a longitudinal direction of the carrier element such as a carrier tape. The piercing movement can, for example, cover an insertion depth of between several tens of micrometers and several millimeters, in particular from 50 micrometers to 5 millimeters, preferably from 0.5 mm to 2.5 mm. The insertion depth can be adjustable over these ranges, it being possible for the adjustability to be provided over the entire range, for example, or over only one or more partial ranges. The piercing movement can in particular be carried out very rapidly, for example at a speed of several meters per second. Alternatively or in addition, the gripper device can be provided to seize at least one test element and, with the latter, carry out at least one sampling movement such as a sample collection movement, for example, to collect a sample from a surface of a user's skin using a test field of the test element. Alternatively, for this purpose, a separate gripper device can be provided.

The gripper device comprises at least one stop element, which is equipped to stop the lancet in the application position and temporarily prevent further movement of the carrier element. This means that the stop element cooperates with the carrier element, and with the lancets arranged on the latter, in such a way that, during transport of the carrier element, a lancet arriving in the application position is in each case stopped, preferably automatically, and is held in the application position. For example, as is explained in more detail below, this stop element can comprise an abutment against which the lancet strikes directly or indirectly, i.e. with interposition of one or more elements, as soon as it reaches the application position. In this way, for example, the carrier element can be subjected to a force that is sufficient to prevent further movement of the carrier element. For example, this force can exceed a maximum force of a slipping coupling of a drive of the carrier element, for example, of a drive of the take-up reel, such that further transport of the carrier element, e.g., the carrier tape, is prevented. The stop element can thus react, for example, to changes of thickness of a lancet tape and, because of this change of thickness triggered by a lancet approaching the application position, prevent further movement of the carrier element.

The gripper device further includes at least one positioning element. This positioning element, which can be designed at least partly separate from the stop element, but which can also be completely or partially integrated with the stop element, is equipped to position the lancet during the piercing movement in at least one direction transverse to a piercing direction. A piercing direction is to be understood as a direction of the piercing movement which, as has been explained above, preferably takes place perpendicularly with respect to a transport direction and/or to a longitudinal direction of the carrier element. A direction transverse to the piercing direction is to be understood as a direction at an angle to this piercing direction, preferably at an angle substantially perpendicular to the piercing direction, although deviations from the perpendicular are also possible, preferably by not more than 20°, in particular by not more than 10°. A positioning of the lancet in at least one direction transverse to the piercing direction can therefore be understood as a positioning of the lancet in such a way that, during the piercing movement, the lancet cannot move or can move only inappreciably in this direction transverse to the piercing direction and/or can change its position and/or orientation in this direction only inappreciably, for example by not more than 1 mm, preferably by not more than 0.5 mm and in particular by not more than 0.2 mm, and/or by not more than 10°, in particular by not more than 5°, and particularly preferably by not more than 3°. The gripper device can in principle have any desired configuration, for example, a diamond shape.

A piercing plane can be defined, for example, by the piercing direction and by a longitudinal direction of the carrier element in the area of the application position. For example, during the piercing movement, the lancet can be positioned by the positioning element in the piercing plane or in a plane parallel to the piercing plane and can in particular be stabilized there. In this way, for example, it is possible to prevent the lancet from lying obliquely with respect to the piercing plane during the piercing movement, for example, as a result of a tensioning of the lancet tape.

For example, an x-direction can be defined by the longitudinal direction of the carrier element in the area of the application position. A y-direction can be defined by the piercing direction itself. In this system of coordinates, the piercing plane represents the x-y plane. The positioning device can, for example, be equipped to hold the lancet during the piercing procedure in this piercing plane or in a plane parallel to this piercing plane. A direction perpendicular to the piercing plane can be defined as the z-direction. Therefore, the positioning device can, for example, be equipped in such a way that the z-coordinate of the lancet and/or at least one point of the lancet is maintained constant during the piercing movement.

The positioning element can in particular comprise at least one holding-down mechanism. A holding-down mechanism is to be understood as an element which is equipped to exert a force on the lancet perpendicularly with respect to a plane, i.e. the piercing plane, formed by the longitudinal direction of the carrier element in the area of the application position and by the piercing direction. For example, the holding-down mechanism can cooperate with a matching element against which the carrier element and/or the lancet are pressed in the application position. The gripper device can include a gripper underpart, wherein the gripper device is equipped to guide the carrier element, for example, the carrier tape with the lancets applied thereon, between the gripper underpart and the positioning element. The gripper underpart can include at least one support surface on which the carrier element is guided. This can be a flat support surface or a curved support surface. The positioning element, for example the holding-down mechanism, can then be equipped to subject the carrier element and preferably the lancet, in the application position, to a force in the direction of the gripper underpart. For example, the holding-down mechanism can be equipped to press the carrier element, e.g., the carrier tape, and/or the lancet against the gripper underpart in the application position, such that the z-coordinate as per the above definition is maintained constant during the piercing procedure.

The stop element of the gripper device can be releasable. This means that the stop element can be changed in terms of its position and/or its orientation and/or its shape such that, after the piercing procedure has been carried out, it can be released in such a way that further movement of the carrier element is again permitted. In an alternative to this preferred embodiment of the stop element as a releasable stop element, it would also be conceivable in principle that, after the piercing procedure has been carried out, the lancet located in the application position is moved in such a way that it is freed.

The stop element can have at least one abutment. This abutment can, for example, comprise at least one abutment edge, preferably a plurality of abutment edges. These abutment edges can, for example, be positioned perpendicularly with respect to the piercing plane. If a plurality of abutment edges are present, they are preferably positioned at an angle to one another. The abutment can in particular be positioned adjacent to the carrier element and be designed such that a lancet is stopped on this abutment during a movement of the carrier element in a transport direction of the carrier element. The lancet can strike directly against this abutment. Alternatively, the lancet can be stopped indirectly by this abutment. For example, the lancet can be covered by at least one film, such that the lancet does not directly strike the abutment, instead the film does. In this case, for example, the change of thickness of the lancet tape, caused by the approaching lancet, can be detected by the abutment and can trigger the stop function.

In addition to the stop function, the abutment can also have further functions, for example, the function, along with the positioning element, of orienting the lancet in such a way that it is possible to compensate for production-related tilting tolerances of the lancet on the carrier element. For example, during production, a tilting of the lancets about an axis perpendicular to the piercing plane can occur. If at least one abutment edge is used, this tilting can be at least partially compensated and the lancet can once again be oriented parallel to the piercing direction.

Particularly if the stop element is designed as a releasable stop element, it is preferable for the abutment to be movable in the direction transverse to a longitudinal direction of the carrier element in the application position, in order to release the stop element. For example, the abutment can be movable substantially perpendicularly with respect to the longitudinal direction of the carrier element, preferably with a deviation of not more than twenty degrees, and particularly preferably of not more than ten degrees, from the perpendicular to the longitudinal direction. The abutment does not necessarily have to be linear or flat, and instead curved abutments are also possible, or an abutment with several lines and/or abutment planes arranged at an angle to one another. Preferably, the abutment is also movable substantially perpendicularly with respect to the piercing direction, such that the abutment is as a whole preferably movable substantially perpendicularly with respect to the piercing plane, in order to release the stop element. Here too, deviations from the perpendicular are again possible, preferably by not more than twenty degrees, and particularly preferably by not more than ten degrees. For example, in order to fulfill the stop function, the abutment can initially be positioned at least partially in the piercing plane, in order to stop a lancet in the application position. After the piercing procedure, the abutment can then be moved out from this plane, in order to release the stop element and free the lancet for further transport of the carrier element, such that a new lancet can be conveyed into the application position.

As has been mentioned above, the gripper device includes at least one stop element, which is equipped to stop the lancet in the application position and temporarily prevent further movement of the carrier element. Moreover, the gripper device can optionally comprise at least one counter-gripper, which can optionally cooperate with the stop element. This cooperation can take place in such a way that the lancet is held with a form fit between the optional counter-gripper and the stop element. Alternatively or in addition, another kind of hold can also be provided, for example, a force-fit hold. However, a form fit is particularly preferable in which, as is explained in more detail below, a holding area of the lancet is received with a form fit between the counter-gripper and the stop element. It is preferably received in such a way that a play for compensation of tolerances in the production and/or the application of the lancet to the carrier element can be compensated.

The optional counter-gripper is preferably designed completely or partially separate from the positioning device, although it can in principle be designed at least partially as a structural part identical with the positioning device. As is explained in more detail below by way of example, the stop element and the counter-gripper are preferably not movable in the transport direction or are movable only inappreciably in the transport direction. However, alternative embodiments are also possible in principle.

The gripper device, in particular the counter-gripper and/or the positioning device, can preferably have at least one ramp, for example, a ramp facing toward the transport element and, e.g., the lancet tape. This ramp can be equipped to allow the lancet to be guided in between the counter-gripper and the stop element. For example, the counter-gripper, the positioning element and the stop element can be arranged on one side of the carrier element, and the above-described optional gripper underpart can be arranged on an opposite side of the carrier element, such that the carrier element with the lancets is guided through and between the gripper underpart and the stop element, the positioning element and the counter-gripper. The counter-gripper can be positioned relative to the stop element in such a way that, during transport of the carrier element in a transport direction, e.g., a spooling direction of a carrier tape in normal operation, the lancet first passes the counter-gripper and then reaches the stop element, so as to abut against the latter. During the movement past the counter-gripper and/or the positioning element, for example, the holding-down mechanism, the ramp can have the effect that a lancet slides more easily under the counter-gripper or the positioning element, in order to reach a gap between the counter-gripper or positioning element and the stop element. The ramp can also be equipped to lift the counter-gripper at least slightly.

The gripper device and/or the lancet device can in particular be designed in such a way that the lancet includes a holding area that can be seized by the gripper device. For example, this holding area can be designed separately from or in one piece with a lancet body, which is intended to be spatially separate from the lancet tip. The holding area can have at least one outer contour allowing the lancet to be subjected to a force parallel to the piercing movement. For example, this contour can have at least one constriction and/or at least one thickening, such that a pushing movement or a pulling movement can be transferred to the lancet by the gripper device even without a force fit, preferably without frictional force. The stop element, and preferably the counter-gripper, can have an inner contour at least approximately matching the outer contour of the holding area. Thus, for example, a gap can be formed between the counter-gripper and the stop element, the inner contour of which gap substantially corresponds at least approximately to the outer contour of the holding area. Tolerances can also be compensated, for example, by means of the inner contour being made slightly larger than the outer contour of the holding area, so as to compensate for, e.g., positioning tolerances and/or orientation tolerances that can arise, for example, in the production and/or application of the lancets.

The gripper device can in particular be designed in such a way that it encloses the lancet or the holding area thereof from several sides, for example, from both sides in the longitudinal direction of the carrier element or from both sides perpendicular to the piercing plane. Accordingly, the gripper device can be designed such that it prevents a tilting of the lancet during the piercing movement.

The lancet can, in some embodiments, be designed such that it has a relatively long lancet tip which protrudes beyond the holding area in the piercing direction. This lancet tip can have an area running to a point or tapering. The lancet tip can be of such a length that it protrudes through a housing opening of a housing of the lancet device and can reach a sufficient insertion depth in a body tissue. In particular, the lancet tip can have a length of more than 2.2 mm, for example, a length of 2.5 mm or more.

In order to stabilize the lancet geometry, the lancet can have a lancet body that runs to a point in the area of the lancet tip and/or toward the front end in the piercing direction. Thus, in addition to having the carrier tape and the lancet elements, the lancet tape can in particular include further elements which, for example, act as a sterile protection for the lancets. This sterile protection can be designed, for example, in the form of another tape, which covers the lancets individually or together. Alternatively or in addition, the sterile protection can also comprise individual coverings for the lancets, for example, pockets or the like. During or before a piercing procedure, for example, the sterile protection can be removed, cut through, punctured, lifted off or otherwise completely or partially removed. The lancet geometry can be configured in such a way, in particular by the above-described stabilization, that there is sufficient stability when the sterile protection is removed. In particular, such a lancet shape, in which the lancet body runs to a point or tapers in piercing direction, for example, starting from the holding area, can be of advantage in lancets whose lancet tip has a length of more than 2.2 mm, in particular of 2.5 mm or more. For example, during the piercing procedure, the tapering or pointed part of the lancet body can emerge through an outlet opening of the lancet device, for example, of a housing of the lancet device, such that the length of the lancet tip can be fully utilized for the piercing procedure. Alternatively or in addition, it is also conceivable that the wall thickness of the housing in the area of the outlet opening is reduced in comparison with an area farther away from the outlet opening, for example, reduced to such an extent that a length of the lancet tip and/or of the tapering or pointed part of the lancet of more than 2.5 mm, in particular of more than 2.2 mm, is substantially not required. Generally, however, it will be noted that other geometries of the lancet can also be used, such that the present invention is generally not limited to a specific lancet geometry.

The gripper device can also include further elements in addition to those elements already described. Thus, the gripper device can, for example, include at least one stationary gripper guide, i.e., a gripper guide which is partially not moved, preferably not moved at all, during the piercing procedure, and in and/or on which at least one non-stationary part of the gripper device is guided. In particular, at least the stop element and preferably also the positioning element and preferably also the counter-gripper can be mounted movably in and/or on the gripper guide. For example, the gripper guide can include one or more rails, in which the stop element and/or the positioning element and/or the counter-gripper are mounted slidably, wherein the rails are preferably oriented in the piercing direction, for example parallel to the piercing direction or at a deviation of not more than 20°, preferably of not more than 10°, from the parallel direction. The gripper guide can, for example, be mounted on a base plate and/or in a housing of the lancet device and/or can be a component part of these elements.

The gripper device can furthermore include at least one gripper spring. This gripper spring can be equipped to subject the stop element and the positioning element and preferably also the optional counter-gripper to a force in the direction of the carrier element. For example, the spring force can act in a direction perpendicular to the piercing plane. In this way it can be achieved that the stop element, in a rest position, is positioned with its at least one optional abutment in such a way that an approaching lancet strikes against this abutment in the application position. To release the stop element, this spring force of the at least one gripper spring can be overcome, for example. The gripper spring can, for example, include at least one leaf spring. For example, one leaf spring can be provided respectively for the stop element and for the positioning element and optionally also for the counter-gripper. However, the gripper spring can also be wholly or partially integrated in one or more of these elements, and/or these elements can themselves be wholly or partially designed as spring elements, as is explained in more detail below. Thus, in particular, the gripper spring can be wholly or partially integrated in the stop element and/or the positioning element and/or the counter-gripper. For example, the stop element and the positioning element and preferably also the counter-gripper can be designed at least in part as spring components. For this purpose, for example, different spring plates and/or parts of one and the same spring plate can be used. Thus, the stop element, the positioning element and the counter-gripper can be worked wholly or partially from a spring plate. For this working, it is recommended to use etching processes and/or cutting processes, for example, a laser cutting process. For example, the spring components, in particular the spring plate, can be wholly or partially arranged parallel to the above-described gripper underpart, for example, to a flat support surface of the gripper underpart. In particular, these spring components can at least almost bear on the gripper underpart, such that the carrier element can be guided between the spring components and the gripper underpart.

The stop element and the positioning element and preferably the counter-gripper can, in principle, be produced from a rigid solid material. Alternatively or in addition, it is also possible for one, some or all of these elements to be designed at least partially as tongues of a spring plate. A spring plate is generally to be understood here as a metallic structural part which is present in plate form, that is to say with a thickness that is considerably smaller than its maximum lateral extent, for example by at least a factor of 10, preferably by at least a factor of 100, and particularly preferably more. In particular, the spring plate can at least in part have elastic properties.

Alternatively or in addition, at least one plastic material can also be used for producing the gripper device. Thus, one or more of the elements gripper spring, stop element, positioning element and counter-gripper can be produced wholly or partially from a plastic material, alternatively or in addition to being wholly or partially produced from a metallic material. In particular, the at least one gripper spring can be produced wholly or partially from at least one plastic material with elastic properties, wherein this at least one gripper spring can also, in turn, be combined wholly or partially with one or more further elements of the gripper device.

The spring plate can have a first tongue acting as stop element, a second tongue acting as the positioning element, in particular the holding-down mechanism, and preferably a third tongue lying opposite the first tongue and acting as the counter-gripper. These tongues can preferably be arranged in the same plane. The second tongue, which acts as the positioning element, can, for example, have at least substantially the shape of the holding area of the lancet. As has been described above, the first tongue, acting as stop element, and the third tongue, acting as counter-gripper, can have between them a gap which, for example, can be filled wholly or partially by the second tongue, which can be bent out from the common plane of the spring plate upon entry of a lancet into the gap, in order to receive the lancet and subject the latter to a force. As has been mentioned above, the second tongue and/or the optional third tongue can have at least one ramp, so as to make it easier to guide a lancet into the gap between the first tongue and the third tongue.

The spring plate can be designed as a flat or bent spring plate. The spring plate should preferably be flat at least in the area of the application position. A bent spring plate can, for example, comprise a U-shaped spring plate.

Other preferred embodiments relate in particular to the lancet device. Thus, the lancet device can further include at least one pierce drive. This pierce drive is intended to be equipped to drive the gripper to perform the piercing movement with the lancet. For possible embodiments of the pierce drive, reference can be made in particular to the document WO 2009/037341 A1 already mentioned above. The drive unit disclosed therein can in principle also be used in the context of the present invention as the pierce drive or as part of the pierce drive. However, other embodiments are also possible in principle.

As has been mentioned above, the stop element can be designed as a releasable stop element. Therefore, if a pierce drive is provided which is equipped to drive the gripper device to perform the piercing movement, this pierce drive can preferably also be equipped to release the stop element after the piercing movement and to free the lancet used beforehand for the piercing movement. As has been mentioned above, this can be achieved by a movement of an abutment of the stop element, for example, a movement with at least one movement component perpendicular to the piercing plane.

This release of the stop element after the piercing procedure, which release is preferably achieved by the pierce drive, can take place in different ways. Thus, for example, the pierce drive can include at least one moving element. Moreover, the pierce drive can have at least one elevation, in particular a ramp and/or a step, wherein the elevation can be connected, for example, to the moving element of the pierce drive. This ramp and/or step can also be designed, for example, as a slide block and/or as another kind of elevation by means of which a release of the stop element is possible. The moving element of the pierce drive can, for example, include a linearly moving element and/or a rotating element. The elevation is equipped to move, for example, lift, at least one abutment of the stop element of the gripper device transversely with respect to a longitudinal direction of the carrier element, e.g., transversely with respect to the piercing plane, so as to release the stop element. For example, the gripper device can be designed in such a way that, after the piercing procedure, and during renewed tensioning of an energy reservoir of the pierce drive, for example, of a pierce spring, at least one elevation formed in the pierce drive, for example, a slide block designed as steps, causes the gripper device, in particular the stop element, to lift at one end, such that the lancet is freed and a transport of the lancet tape or carrier tape can take place. The positioning element, in particular, the holding-down mechanism, can facilitate the release of the lancet from the gripper device in the transport direction. During the transport of the carrier tape, the gripper device can be wholly or partially spring-mounted on the lancet tape or the carrier tape. The resulting friction can be minimized such that the transport of the carrier tape or of the lancet tape is not substantially impeded.

The pierce drive can, for example, have at least one driving disk as the moving element. An axis of this driving disk can preferably be arranged transversely, in particular at least approximately perpendicularly, with respect to a transport direction of the carrier element in the area of the application position. For example, this axis can be arranged substantially perpendicularly with respect to the piercing plane or substantially in the piercing plane or parallel to the piercing plane. As with all the angles indicated in the context of the present invention, "substantially" means that it is also possible to tolerate deviations of preferably not more than 20°, particularly of not more than 10°, particularly preferably of not more than 5°, and particularly preferably zero. If such a driving disk is provided, this driving disk can, for example, have the elevation arranged on its circumferential side and/or on its flat side, for example, the ramp and/or the step which is equipped to release the stop element. Thus, for example, by means of this at least one elevation, the abutment can be moved, e.g., lifted, with at least one movement component perpendicular to the piercing plane, in order to release the lancet. Alternatively or in addition to a driving disk, however, other moving elements are also possible in the pierce drive. For example, drive rods or other kinds of drives can be used alternatively or in addition. Movable elements of this kind can also be designed with one or more corresponding elevations for releasing the stop element.

Compared to known devices of this kind, the proposed gripper device and the lancet device in one or more of the described embodiments have numerous advantages. For example, a particularly space-saving gripper device can be achieved, which can also be easily integrated in compact lancet devices. Integration in combined appliances, for example, hand-held appliances, is also possible, that is to say in appliances which, in addition to the lancet function, have at least one analysis function.

The proposed gripper device is also very suitable for compensation of production-related tolerances, for example, tolerances that arise during the production of the lancets and/or the connection of the lancets to the carrier element. For example, if a tape magazine with a lancet tape is used, the demands on the manufacturing process of this tape magazine are reduced considerably.

Moreover, different functions can be combined in the gripper device. Thus, the spring function, holding and/or gripping function and stop function can be integrated, as a result of which the overall size can be further reduced. Moreover, an optimized lancet geometry can be realized in combination with the gripper. In this way, deviations in a manufacturing process can also be compensated, and a higher degree of system safety can be obtained. The described gripper device can cooperate in a simple way with the pierce drive of the lancet device, and the pierce drive can also be wholly or partially integrated in the gripper device itself.

BRIEF DESCRIPTION OF THE DRAWINGS

Further details and features of the invention will become clear from the following description of preferred illustrative embodiments. The respective features can be embodied singly, or several of them in combination with one another. The invention is not limited to the illustrative embodiments. The illustrative embodiments are shown schematically in the figures. Identical reference numbers in the individual figures designate elements which are identical or whose functions are identical or which correspond to one another in terms of their functions.

FIGS. 7A to 11B show different method steps in a piercing procedure using the lancet device and gripper device shown in FIG. 4; and FIGS. 12A to 16B show different method steps in a piercing procedure using the variant of the sheet-metal component shown in FIG. 6.

DETAILED DESCRIPTION

Figure 1:
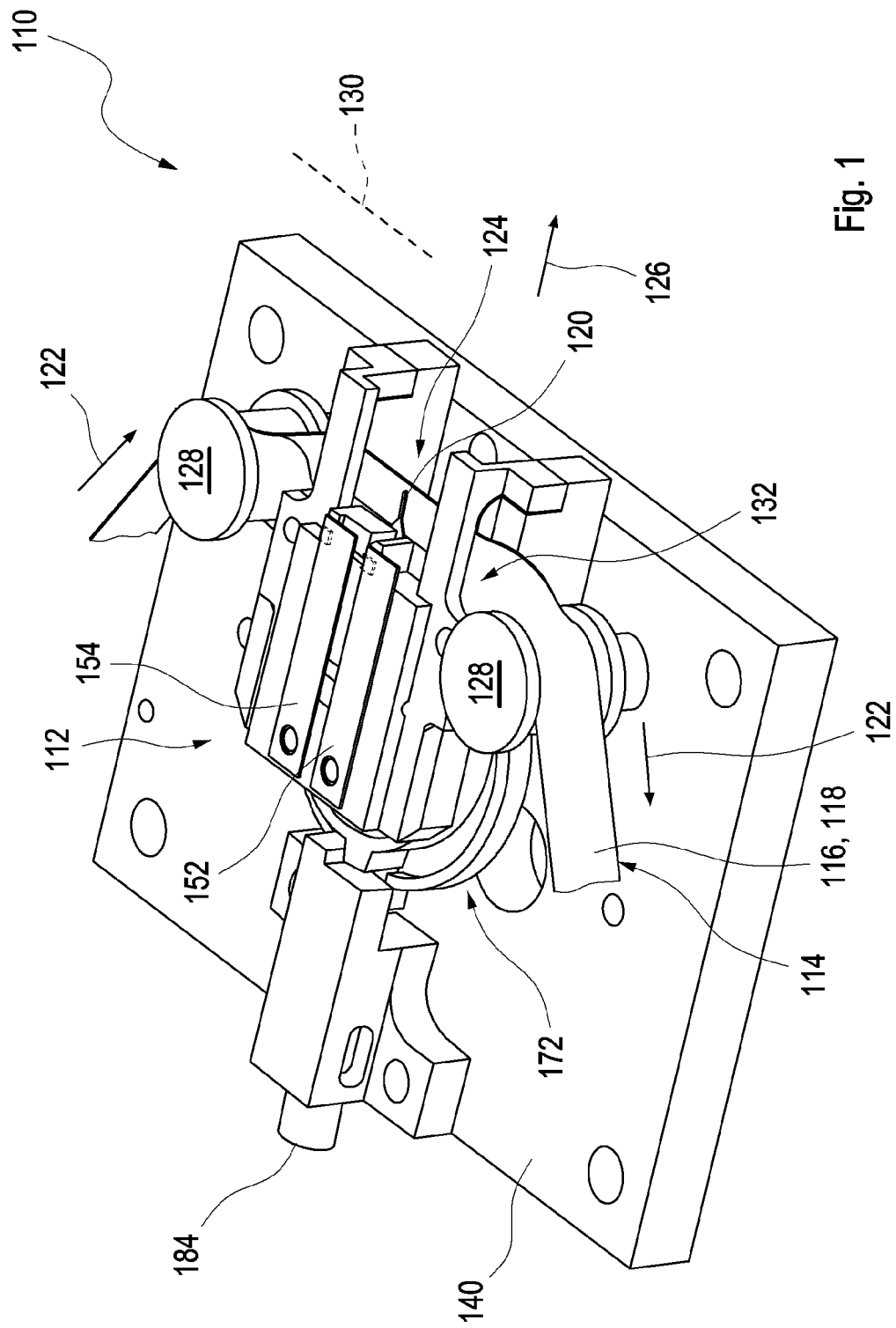
FIG. 1 shows a perspective view of a first illustrative embodiment of a lancet device with a gripper device.
Figure 2:
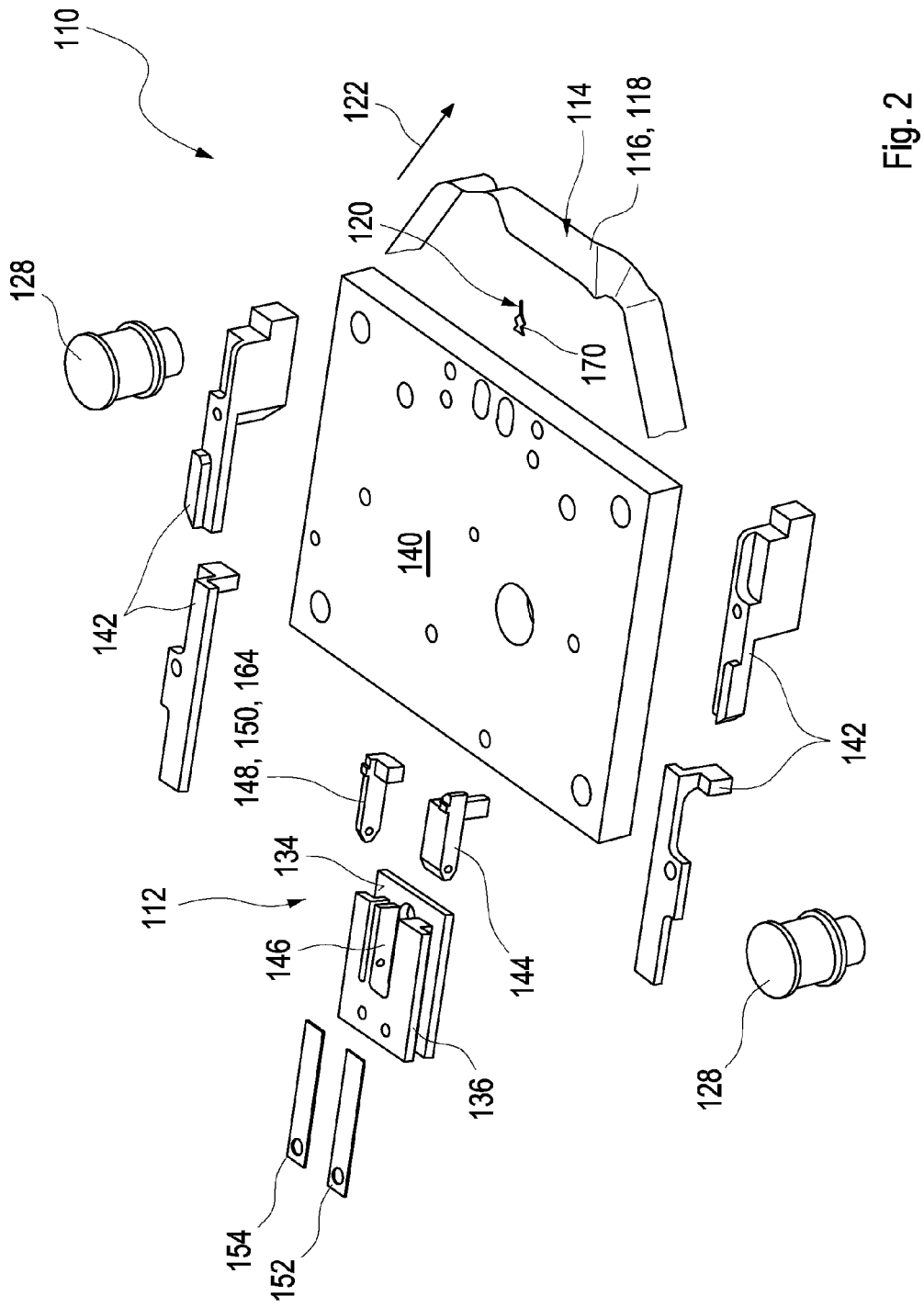
FIG. 2 shows the lancet device from FIG. 1 in an exploded view.
Figure 3:
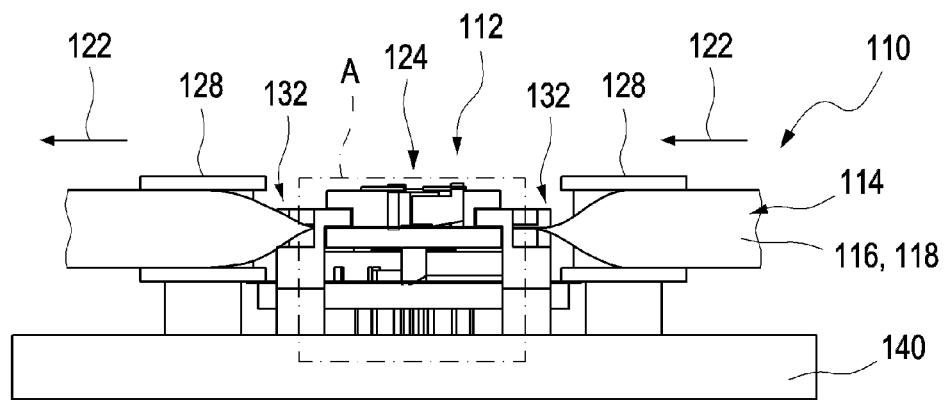
FIGS. 3A and 3B show details of the gripper device of the lancet device from FIG. 1.
Figure 3:
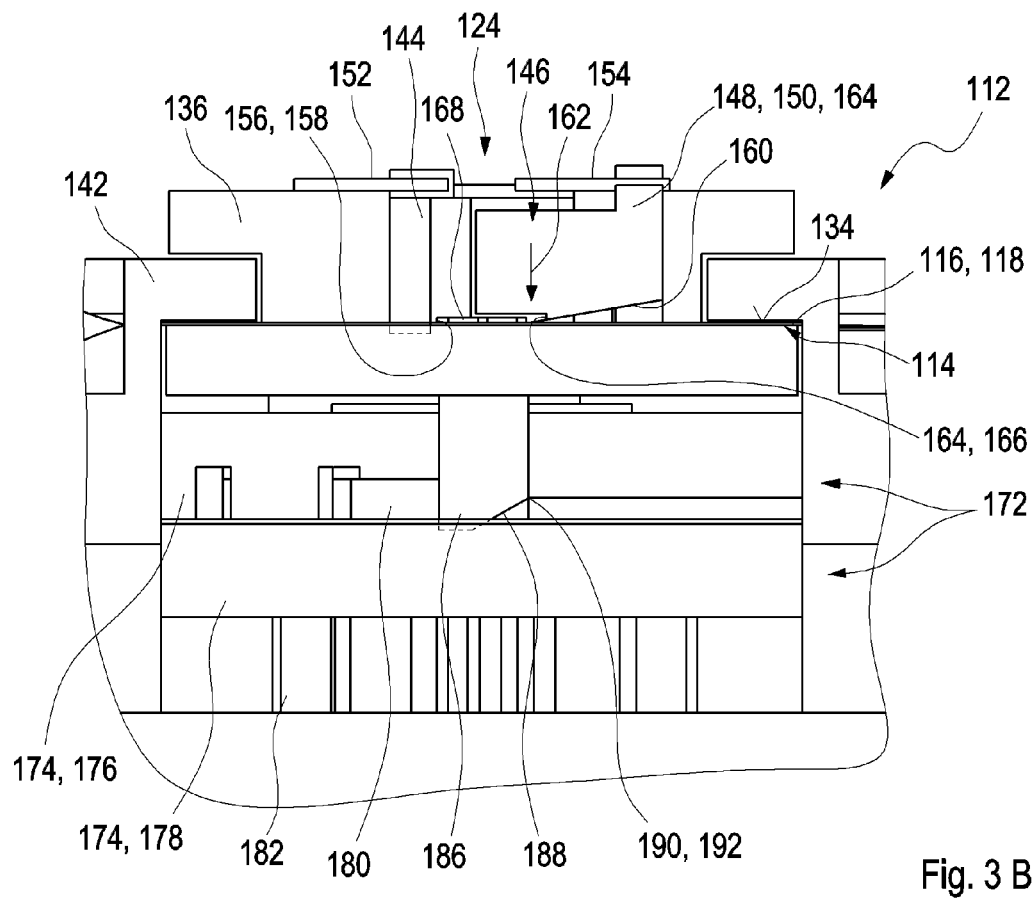

FIGS. 1 to 3B show a first illustrative embodiment of a lancet device 110 with a gripper device 112. Of these, FIG. 1 shows a perspective view of parts of the lancet device 110. FIG. 2 shows an exploded view of parts of the lancet device 110 from FIG. 1, in particular of parts of the gripper device 112. FIG. 3A shows a front view of the lancet device 110, looking toward the gripper device 112, and FIG. 3B shows an enlarged view of the area of the gripper device 112 that is boxed-in and indicated by A in FIG. 3A. All of the FIGS. 1 to 3B will be explained jointly hereinbelow. It should be noted that the lancet device 110 can contain numerous other elements not shown in FIGS. 1 to 3B. Thus, in particular, a housing can also be provided, which can enclose all or some of the components shown in FIGS. 1 to 3B.

In the illustrative embodiment shown, the lancet device 110 comprises a lancet tape 114. This lancet tape 114 in turn comprises a carrier element 116 in the form of a carrier tape 118, on which a plurality of lancets 120 are applied. Here, "applied" is to be understood not only as meaning the possibility of the lancets 120 being placed on a surface of the carrier tape 118, but also the possibility of the lancets 120 being embedded between several elements of the carrier element 116, for example between several layers. The carrier tape 118 can, for example, be designed as a plastic and/or paper tape. For example, the lancets 120 can be arranged between at least two tapes of the carrier tape 118, in which case at least one of the tapes can serve as the actual carrier and at least a second one can serve as a covering. Together, the tapes can form a tight pack and keep the lancets 120 sterile.

The carrier tape 118 can, for example, be provided from a supply reel (not shown in the figures), spooled through the lancet device 110 in a spooling direction 122 and, finally, wound onto a take-up reel (also not shown). The take-up reel, for example, can be driven for the purpose of the spooling procedure.

By means of this spooling mechanism, the lancets 120 are provided in succession in an application position 124 of the lancet device 110, are seized there by the gripper device 112 and are used for a piercing movement in a piercing direction designated in FIG. 1 by reference number 126. For this purpose, the carrier tape 118 is preferably deflected upstream and downstream of the application position 124 by means of guide rollers 128, such that the carrier tape 118, at least in the area of the application position 124, has a longitudinal direction indicated symbolically in FIG. 1 by reference number 130, which direction is preferably substantially perpendicular to the piercing direction 126. As has been explained above, however, slight deviations from this perpendicular are also possible. The longitudinal direction 130 and the piercing direction 126 together define a piercing plane. By means of a tape deflection 132, the carrier tape 118 can be deflected or curved around in the area of the application position 124 in such a way that it extends substantially parallel to this piercing plane in the area of the application position 124. This can be seen particularly clearly in the exploded view according to FIG. 2 or in the front view according to FIG. 3A. During the spooling procedure, the lancet tape 114 runs on a support surface 134 of a gripper underpart 136. This can be seen particularly clearly in the views according to FIGS. 2 and 3B. The gripper underpart 136, which can be designed in one piece or also in more than one piece, has a guide groove 138 which, in this illustrative embodiment, accommodates a gripper guide 142 (see also the detailed view in FIG. 3B) which is mounted in a stationary position with respect to a carrier plate 140 or to a housing or housing part of the lancet device 110. In this way, by means of the gripper guide 142, the gripper device 112 or a part thereof is mounted movably in the piercing direction 126 and can carry out the piercing movement.

In the illustrative embodiment shown, the gripper device 112 has a multi-part construction, which will be explained with reference to the detailed view in FIG. 3B. Thus, the gripper device 112 has a stop element 144, which is mounted pivotably in a seat 146 of the gripper underpart 136 such that it can execute a pivoting movement, with its part protruding farthest in the piercing direction 126, about a pivot axis that is arranged, for example, in the piercing plane. Similarly, a positioning element 148 in the form of a holding-down mechanism 150 is mounted pivotably in the seat 146, for example about the same pivot axis as the stop element 144. The stop element 144 and the holding-down mechanism 150 are urged toward the lancet tape 114 by separate gripper springs 152, 154 with a spring force perpendicular to the piercing plane.

In the illustrative embodiment shown, the stop element 144 has an abutment 156 in the form of an abutment edge 158. During the spooling of the lancet tape 114, the stop element 144 is pressed downward by the gripper spring 152 against the lancet tape 114, such that a lancet 120 (not shown in FIG. 3B) that has arrived at the application position 124 strikes against the abutment 156. Further spooling of the lancet tape 114 is stopped in this way. For example, a drive of the take-up reel can be designed such that the latter has a slipping clutch, which slips on account of the increased torque applied when a lancet 120 in the application position 124 reaches the abutment 156. In this way, a residual run of a lancet tape drive can be continued without this damaging the lancet tape 114.

The positioning element 148 in the form of the holding-down mechanism 150 has a ramp 160 for guiding in the lancet tape. This ramp 160 has the effect that, as the lancet 120 is being guided in, the holding-down mechanism 150 is lifted counter to the force of the gripper spring 154, such that the lancet 120 can move to the stop element 144. In the application position 124, the lancet 120 is then subjected by the positioning element 148 to a force 162 acting perpendicularly with respect to the piercing plane (which in FIG. 3B runs horizontally and perpendicularly with respect to the plane of the drawing) and is thus held in the piercing plane or in a plane parallel to the piercing plane.

Moreover, as in the illustrative embodiment in FIGS. 1 to 3B, the gripper device 112 can optionally have a counter-gripper 164. In the illustrative embodiment shown, this counter-gripper 164 is formed in one piece with the positioning element 148, although it can also be designed as a separate component. The ramp 160 can accordingly also be part of the counter-gripper 164. In the illustrative embodiment shown, the counter-gripper 164 has an edge 166 lying opposite the abutment edge 158. Between the edge 166 and the abutment edge 158, a gap 168 is formed in which a holding area 170 of the lancet 120 is received when the lancet 120 has arrived at the application position 124. The holding area 170 can have a contour which, apart from possible tolerances and a tolerance compensation, can match the outer contour of the holding area 170. Examples of such a contour are explained in more detail in subsequent illustrative embodiments.

The lancet device 110 moreover comprises a pierce drive 172. This pierce drive 172 can be completely or partially coupled to a tape drive of the lancet device 110. An illustrative embodiment of the pierce drive 172 will be explained with reference to FIG. 3B.

Thus, in the illustrative embodiment shown, the pierce drive 172 has a multi-part driving disk 174. The latter in turn has a gripper driving disk 176, coupled to the gripper underpart 136, and a tensioning disk 178 arranged underneath this gripper driving disk 176. The gripper driving disk 176 and tensioning disk 178 can be coupled to each other via a pierce spring 180, for example in the form of a spiral spring. The coupling between the gripper driving disk 176 and the gripper underpart 136 can be effected, for example, via a cam (not shown in FIG. 3B) on the gripper driving disk 176, wherein the cam engages in a corresponding groove on the underside of the gripper underpart 136.

In a spooling procedure, during which the lancet tape 114 is advanced incrementally, the tensioning disk 178 is rotated, for example by means of a toothed wheel 182 on the underside of the tensioning disk 178. The gripper driving disk 176 is not rotated therewith, or not fully rotated therewith, such that the pierce spring 180 is tensioned. By means of a trigger mechanism 184, the gripper driving disk 176 is held in the tensioned state.

At the same time, during this slow movement of the tensioning disk 178, the lancet tape 114 is advanced incrementally. A lancet 120 slides under the ramp 160, briefly lifts the holding-down mechanism 150 and, finally, is stopped on the abutment 156 of the stop element 144. The holding-down mechanism 150 moves back down, such that the lancet 120 in the application position 124 is received in the gap 168. At the same time, as has been described above, the pierce spring 180 is tensioned during this procedure. After the trigger mechanism 184 has been triggered, the gripper driving disk 176 and/or the pierce spring 180 are freed by the trigger mechanism 184, and the gripper driving disk 176 can execute a rapid rotation movement, during which the gripper underpart 136 along with the stop element 144 and the positioning element 148 and optionally along with the counter-gripper 164 is driven in a rapid piercing movement in piercing direction 126 and in a subsequent return movement. The pierce spring 180 is thus relaxed. After this piercing procedure, the lancet tape 114 can be advanced in the spooling direction 122. For this purpose, the stop element 144 is releasable, in order to permit further transport of the lancet tape 114. In the illustrative embodiment shown, the stop element 144 for this purpose has a continuation 186, which protrudes downward through a passage in the gripper driving disk 176 and has a ramp 188. This continuation 186 cooperates for its part with a ramp 190 or a step 192 on the tensioning disk 178 and/or other parts of the driving disk 174. If the tensioning disk 178 is rotated during the advance movement, the stop element 144 is lifted by this ramp 190 or step 192 by means of the continuation 186, such that the lancet 120 is freed from the gap 168 and further advance movement is permitted. For example, this lifting of the stop element 144 by the ramp 190 or step 192 can take place for a maximum rotation angle of thirty degrees of the tensioning disk 178. The step 192 or the ramp 190 then ends again, and the stop element 144 moves back down, such that the gripper closes again. To ensure that the lancet 120 is not moved along in the lifting movement of the stop element 144, the lancet can continue to be pressed down by the holding-down mechanism 150 during this opening procedure or at least during a period of this lifting procedure. All the parts of the gripper can be acted on permanently by the gripper springs 152, 154, which can be designed, for example, as leaf springs.

Figure 4:
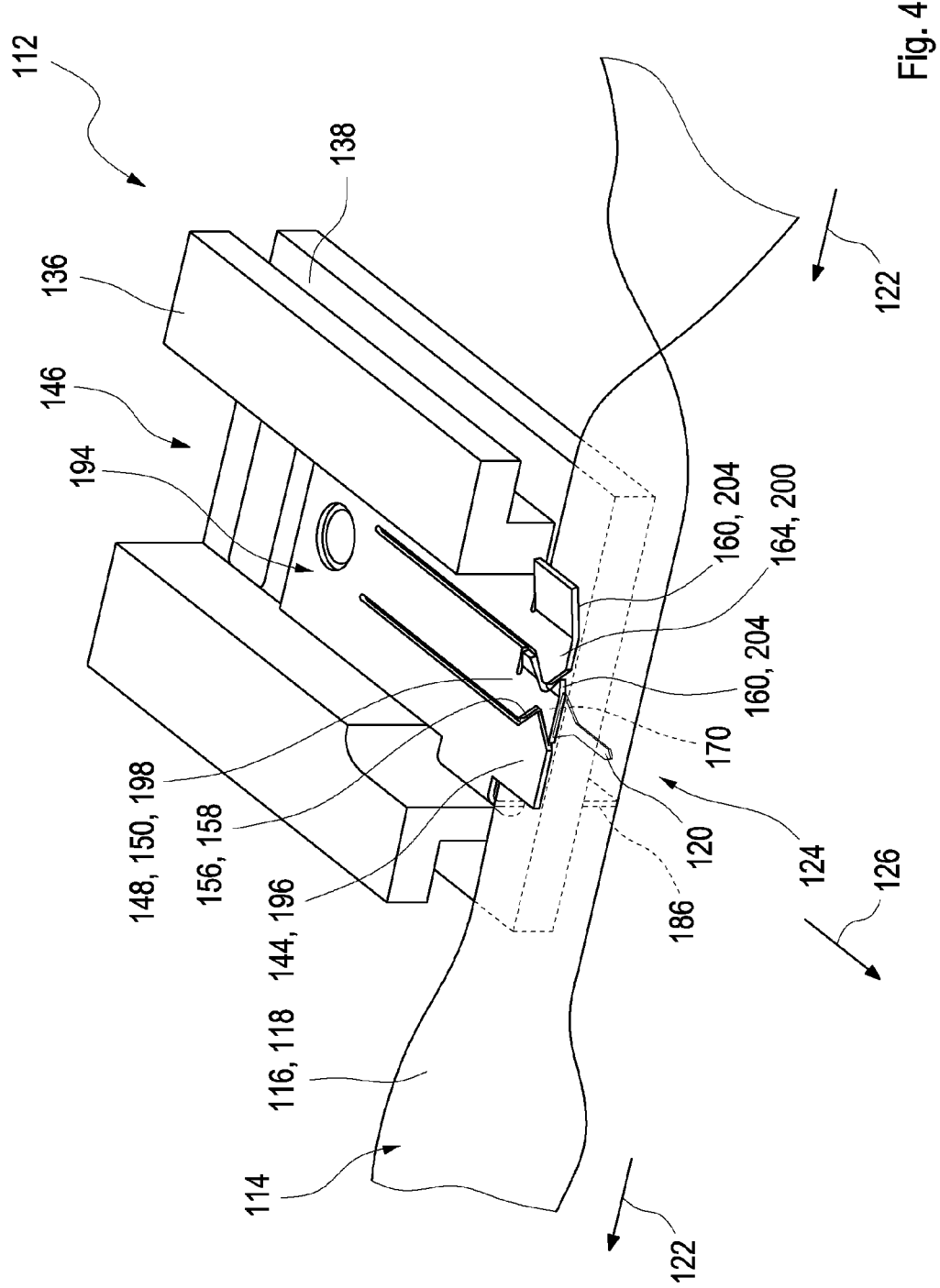
FIG. 4 shows an alternative illustrative embodiment of a gripper device with a sheet-metal component.

In the illustrative embodiment according to FIGS. 1 to 3B, the actual gripper of the gripper device 112 thus consists of the stop element 144, the positioning element 148 and optionally the counter-gripper 164, and also the associated gripper springs 152, 154. The gripper forms the movable parts of the gripper device 112 which allow a lancet 120 to be seized in the application position 124. This at least five-part design of the actual gripper can be greatly simplified by means of these components being wholly or partially combined. Thus, FIG. 4 shows an alternative illustrative embodiment of the gripper device 112, in which these parts of the gripper, plus the gripper underpart 136, can be reduced to two parts. First, a gripper underpart 136 is once again provided, which can be designed similarly to the gripper underpart 136 in the illustrative embodiment according to FIGS. 1 to 3B and which, for example, can once again have a guide groove 138. However, instead of the various individual elements 144, 148, 164, 152 and 154 mentioned above, a single gripper plate 194 or several such gripper plates 194 is/are integrated in a seat 146 of this gripper underpart 136. This gripper plate is designed as a spring plate and has a first tongue 196, a second tongue 198 and a third tongue 200. While the first tongue 196 has an abutment 156 and acts as stop element 144, the middle and second tongue 198 act as positioning element 148 and holding-down mechanism 150. For its part, the third tongue 200, arranged farthest counter to the spooling direction 122, has an edge 160 lying opposite the abutment edge 158 and acts as counter-gripper 164. The gripper plate 194 can be connected to the gripper underpart 136 via a fixing means 202, for example. The spring action, which was originally applied by the gripper springs 152, 154, can now be integrated in the gripper plate 194 by virtue of at least partial elastic properties of the gripper plate 194, which can be designed as a spring plate.

Moreover, the gripper plate 194 can be bent and, at its side arranged farthest in the spooling direction 122, can have a downwardly protruding continuation 186. Also, at the side arranged farthest counter to the spooling direction 122, the counter-gripper 164 can have a ramp 160 which, in the configuration as gripper plate 194, can be designed simply in the form of an upwardly bent tab 204. The configuration of the gripper plate 194 can have substantially the same function as in the illustrative embodiment described in FIGS. 1 to 3B. Thus, as regards the sequences in the procedure for advancing a lancet 120, reference can largely be made to the above description.

Figure 5:
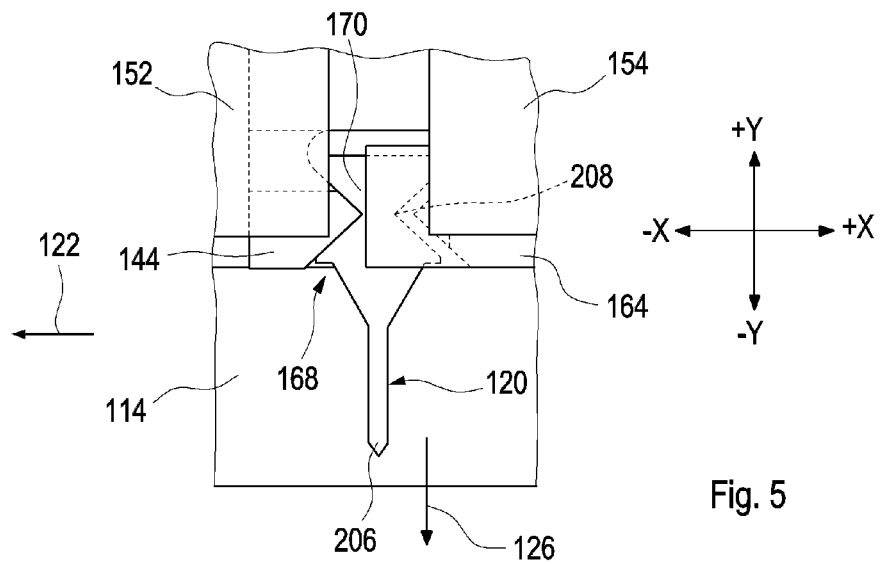
FIG. 5 shows a detail of a form-fit connection between the gripper device from FIG. 4 and a lancet.

The novel geometry of the gripper device 112 according to the first or the second illustrative embodiment permits the provision of a form-fit gripper, as an alternative or in addition to a force-fit gripper. This is shown by way of example in FIG. 5. FIG. 5 shows a lancet 120 viewed in a piercing plane. The lancet 120 has a lancet tip 206 and a holding area 170. For its part, the holding area 170 has a contour that allows the lancet 120 to be seized with a form fit by the gripper device 112. Thus, the holding area 170 has an outer contour with a constriction 208. A gap 168 between the stop element 144 and the counter-gripper 164 can for its part have an inner contour which, apart from positioning tolerances and/or manufacturing tolerances, can correspond substantially to the outer contour of the holding area 170.

In the view according to FIG. 5, the longitudinal direction of the lancet tape 114 defines an x-direction, whereas the piercing direction 126 defines a y-direction. The novel lancet geometry provides a form-fit gripper which ensures that, during the piercing procedure, the lancet 120 cannot deviate either in the +/−x-direction or in the +/−y-direction. A movement in a +/−z-direction, which is defined as a direction perpendicular to the piercing plane, is excluded or at least substantially prevented by the holding-down mechanism 150 (not shown in FIG. 5). Tolerances of the kind that can arise, for example, during a manufacturing process in applying the lancet, can be compensated in the +/−y-direction and also in the +/−x-direction.

Figure 6:
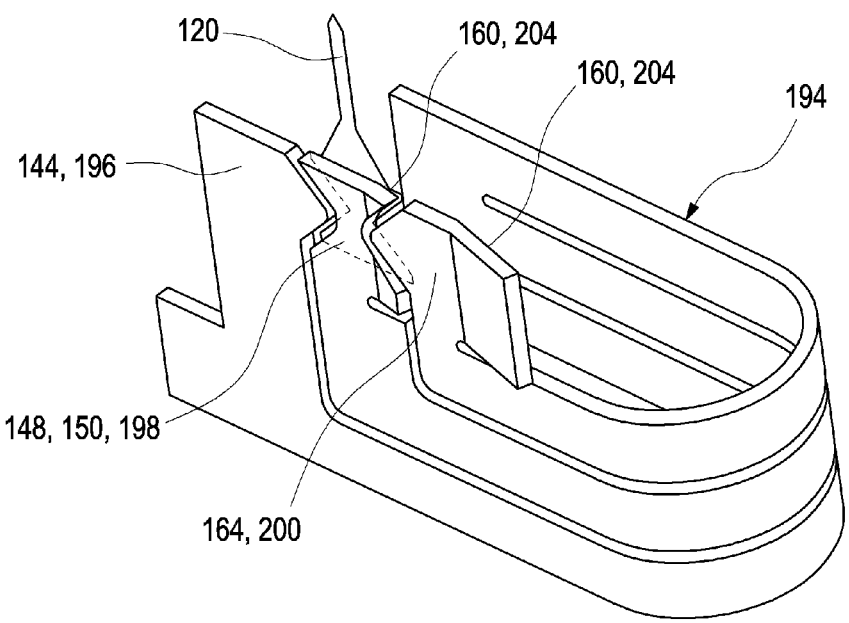
FIG. 6 shows an alternative illustrative embodiment with a curved sheet-metal component.
Figure 7:
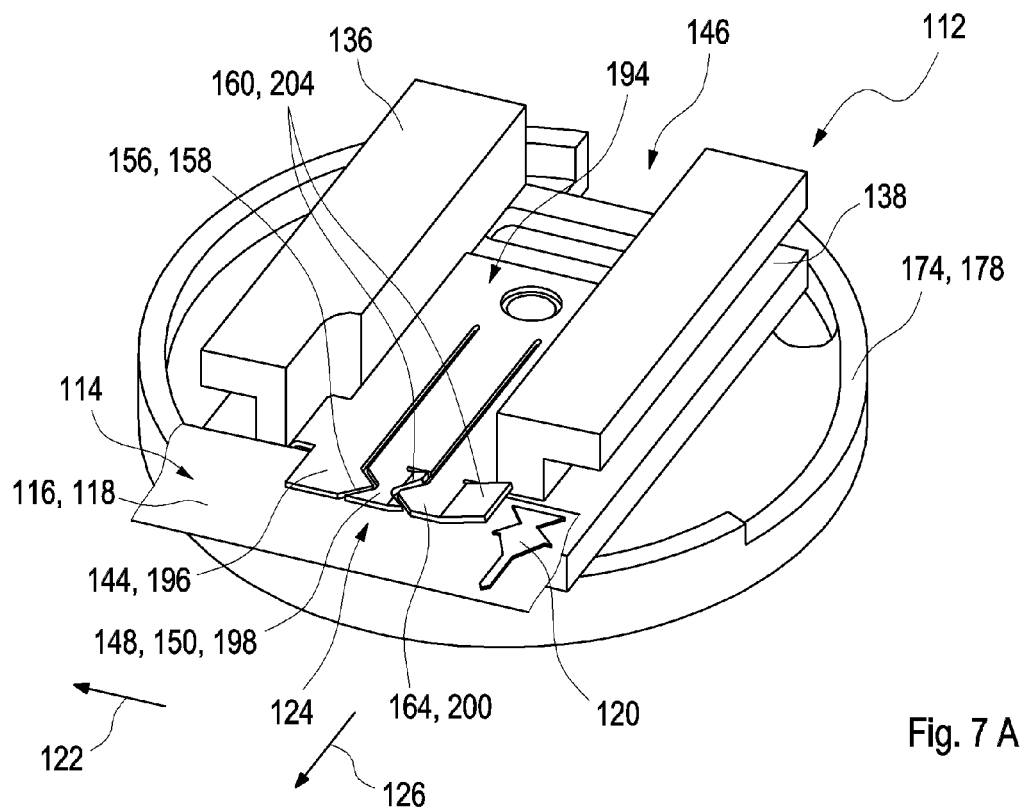
Figure 7:
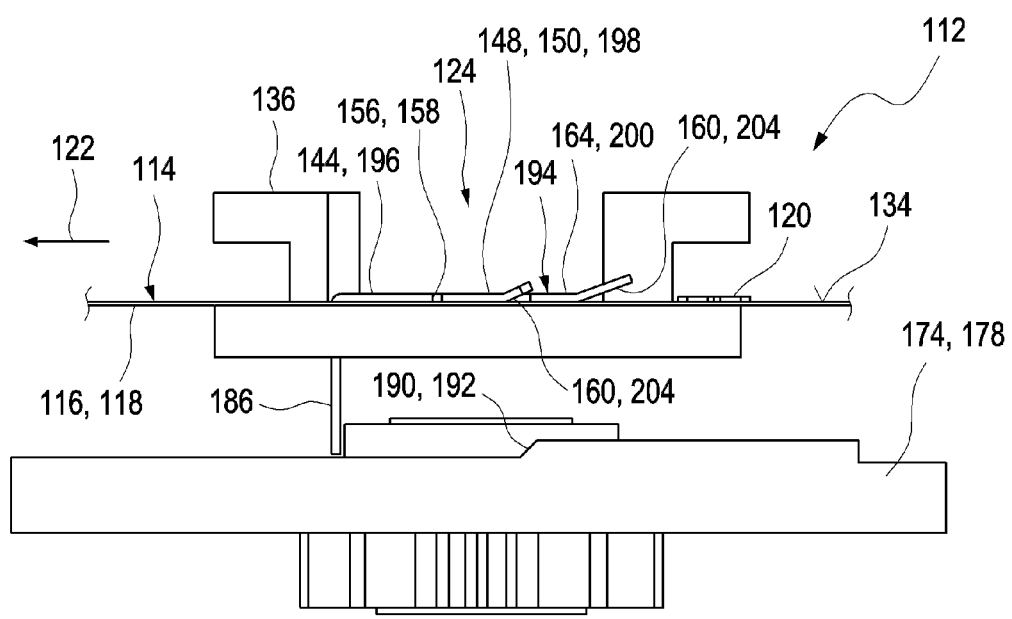
Figure 8:
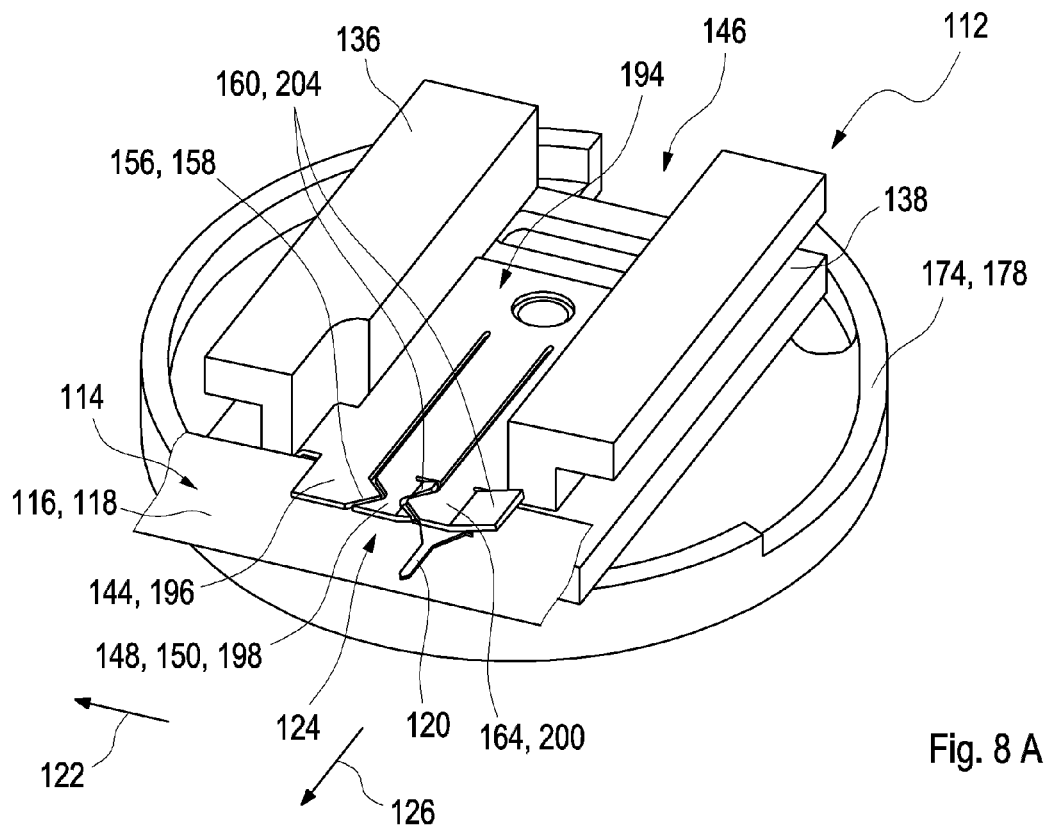
Figure 8:
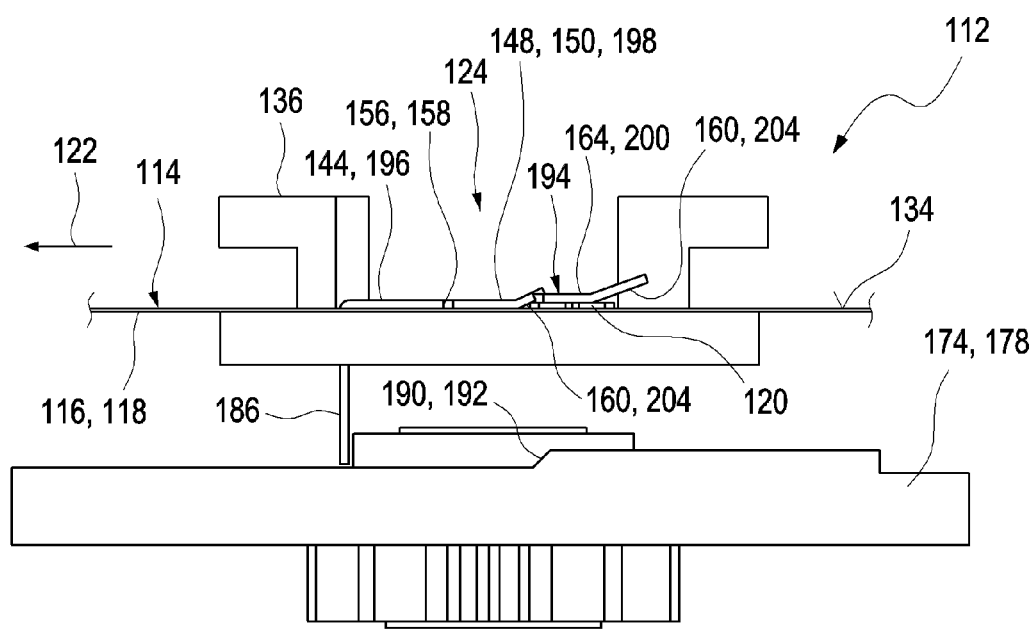
Figure 9:
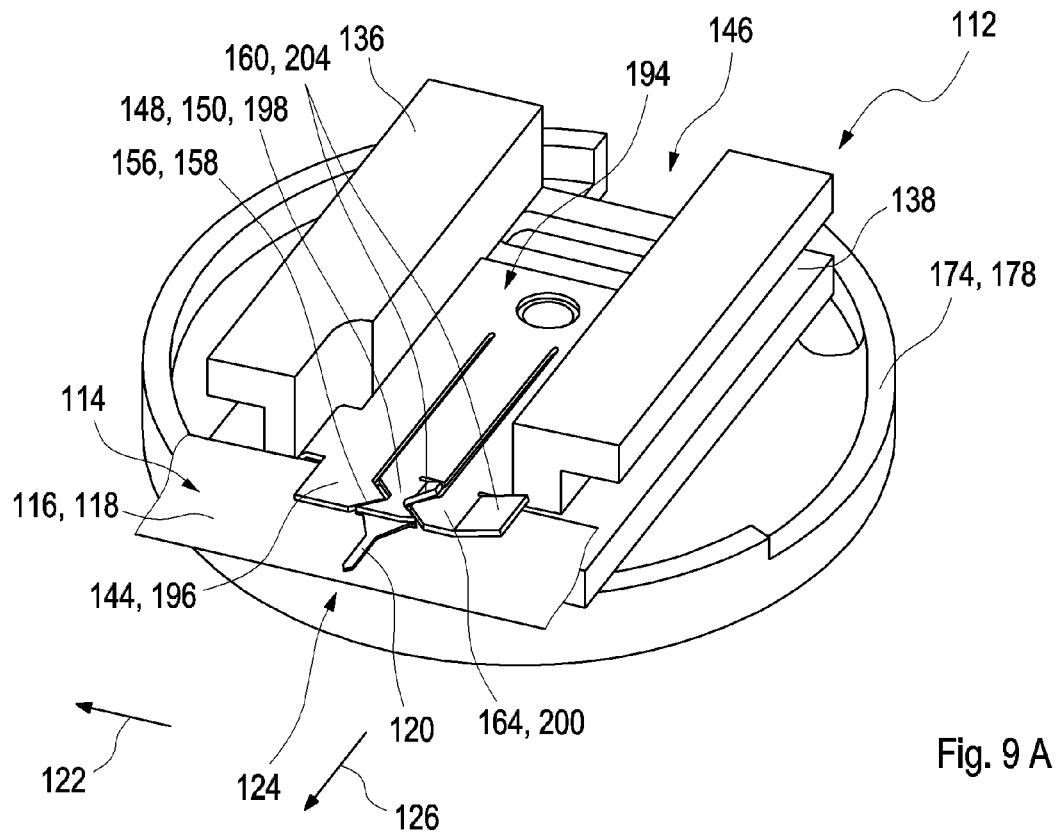
Figure 9:
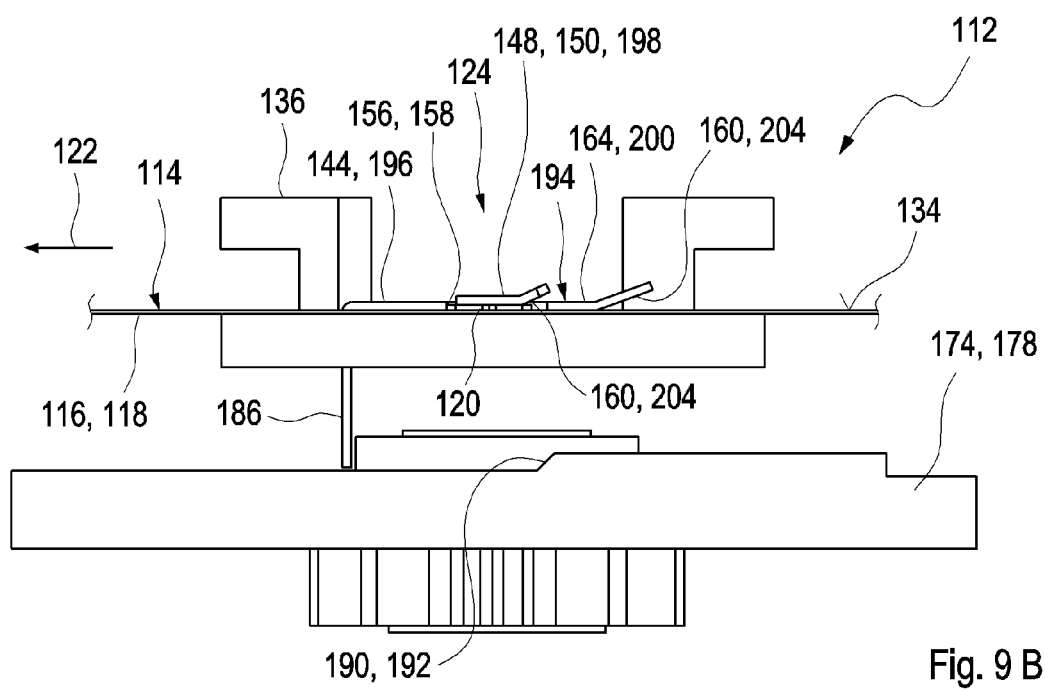
Figure 10:
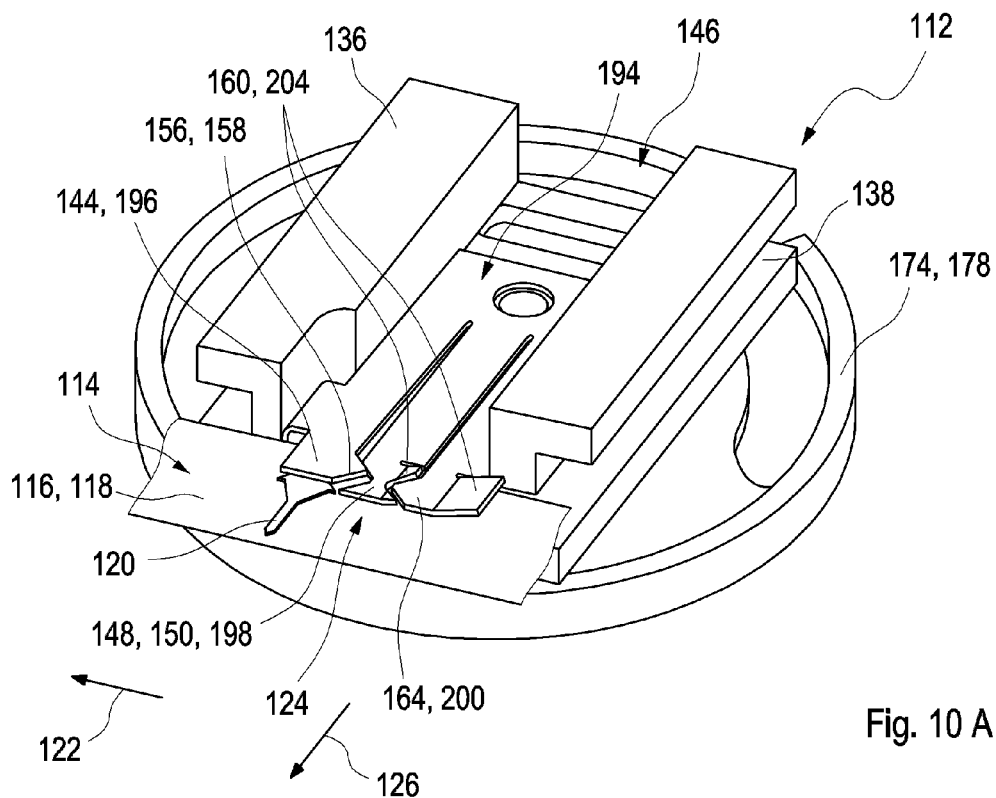
Figure 10:
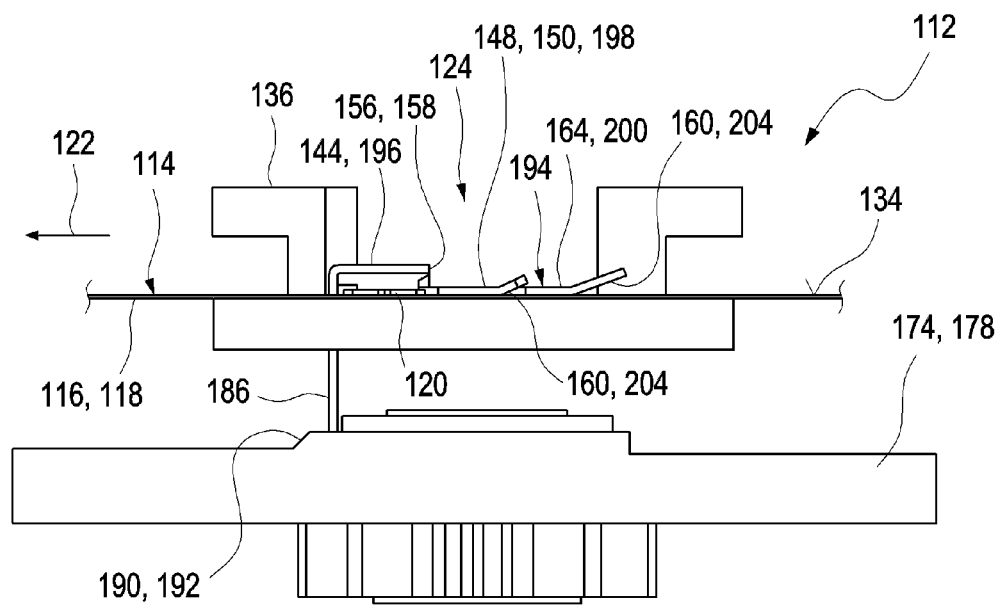
Figure 11:
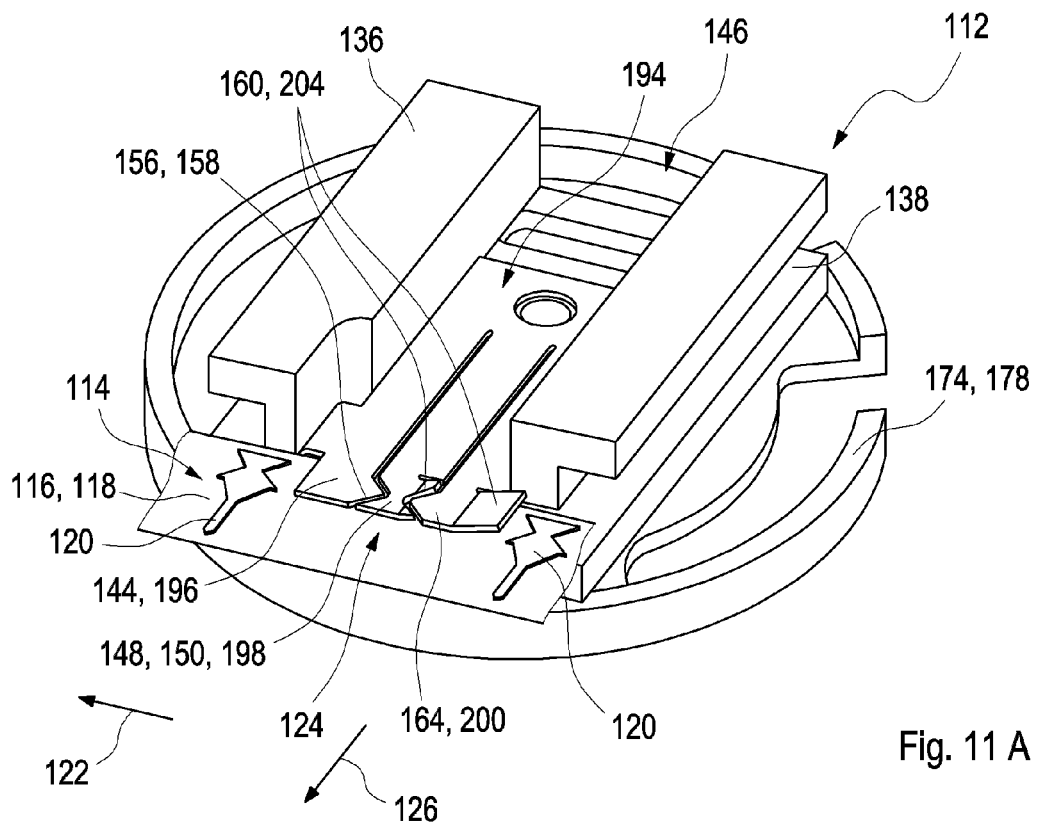
Figure 11:
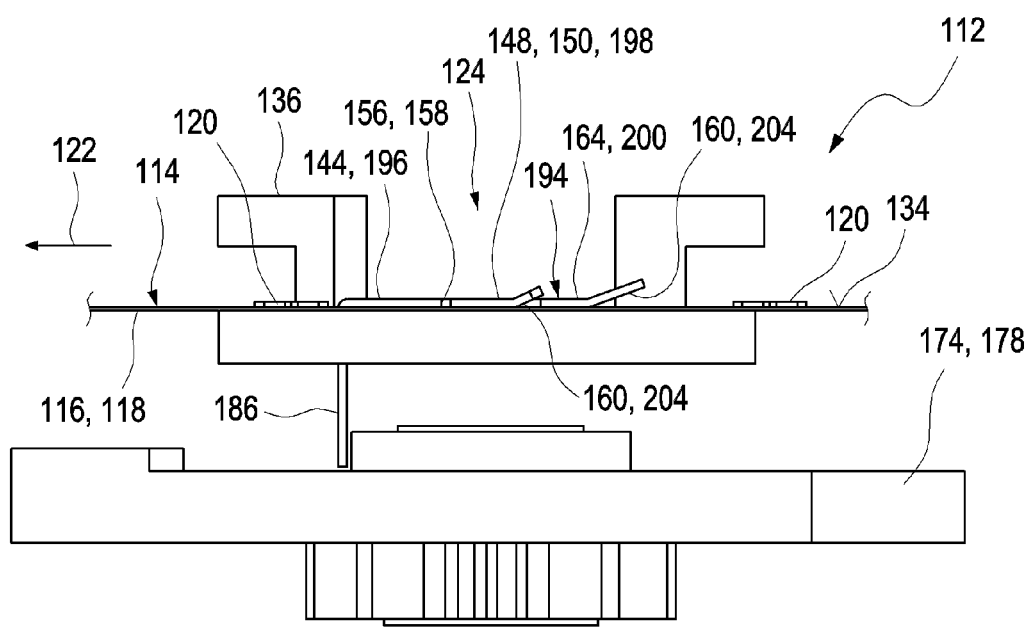
Figure 12:
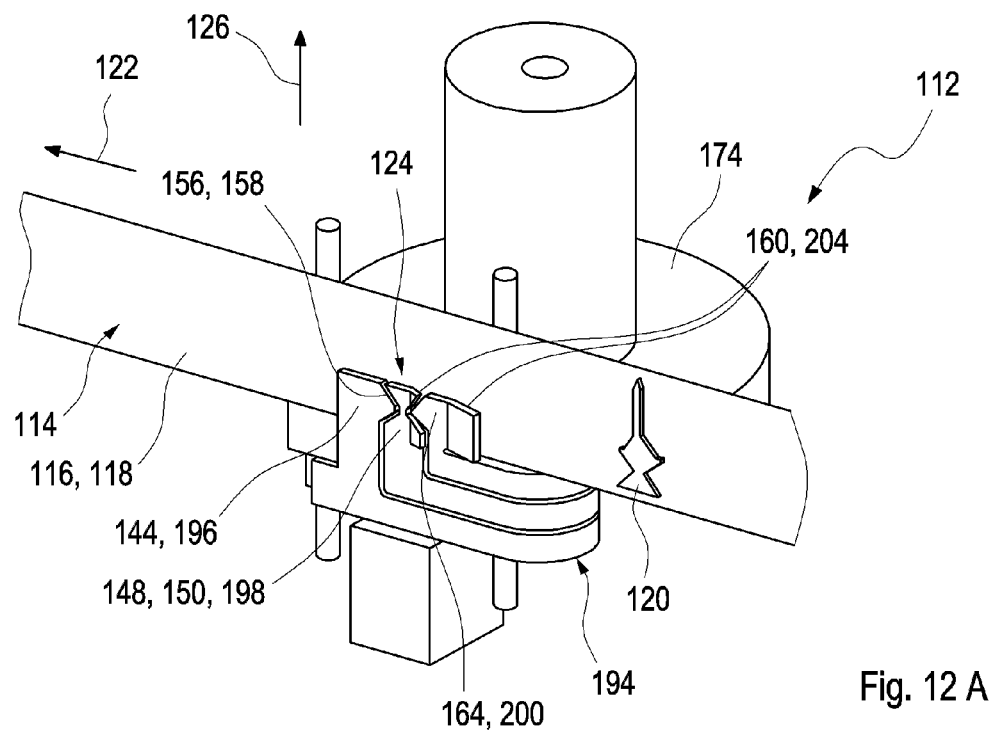
Figure 12:
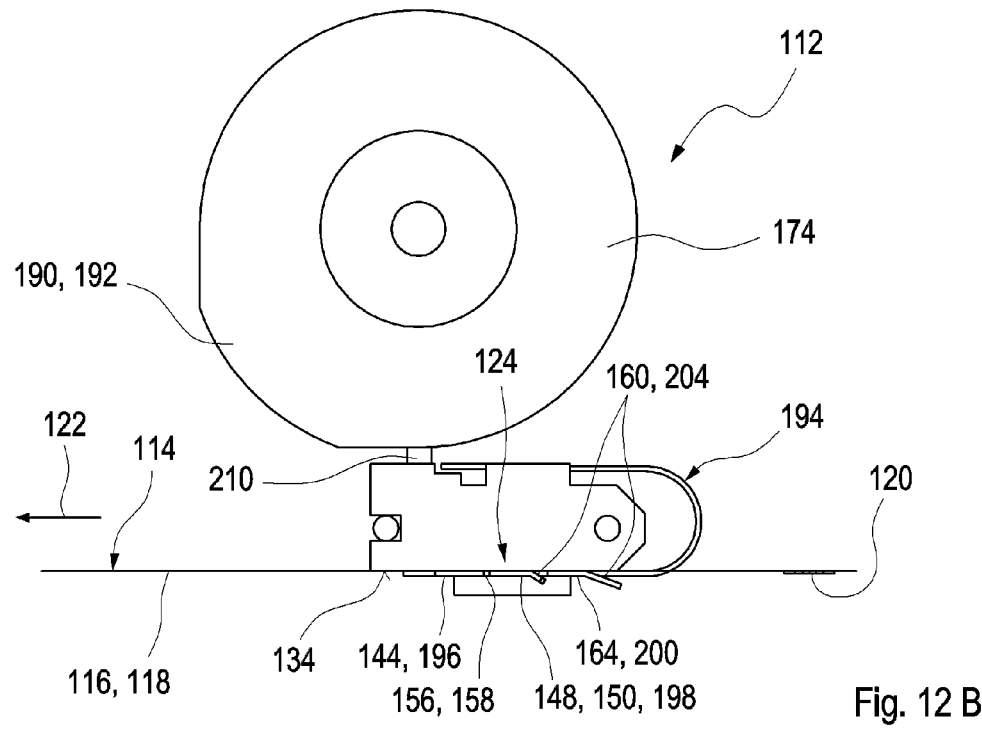
Figure 13:
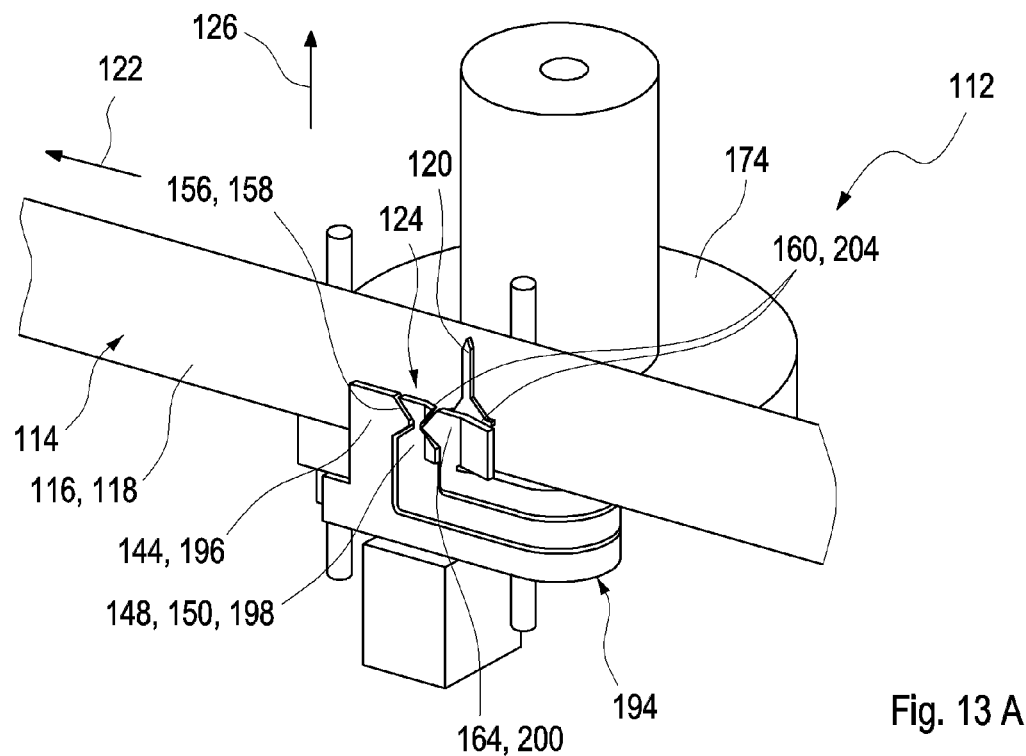
Figure 13:
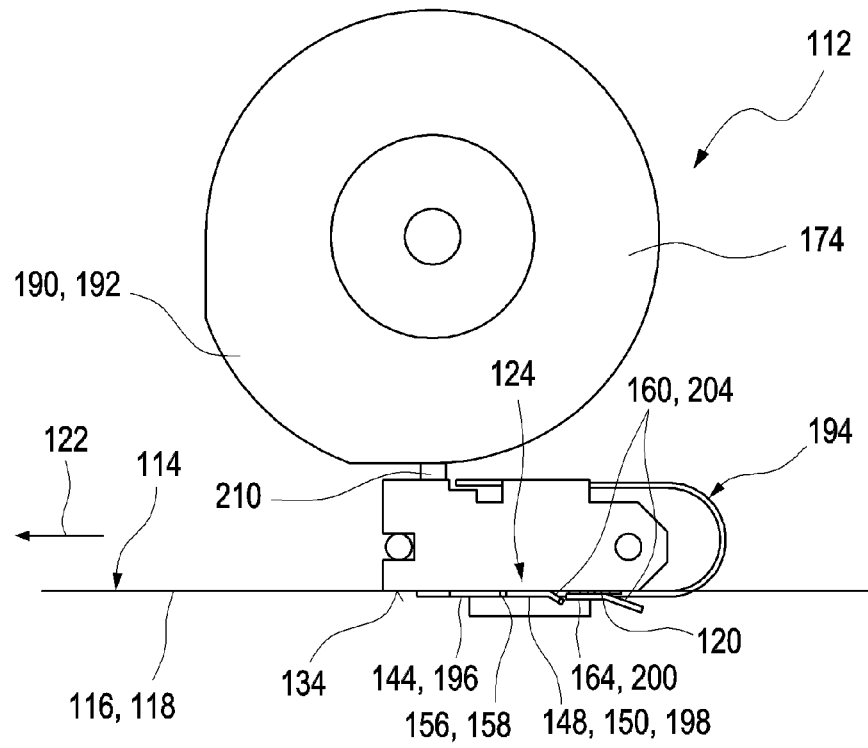
Figure 14:
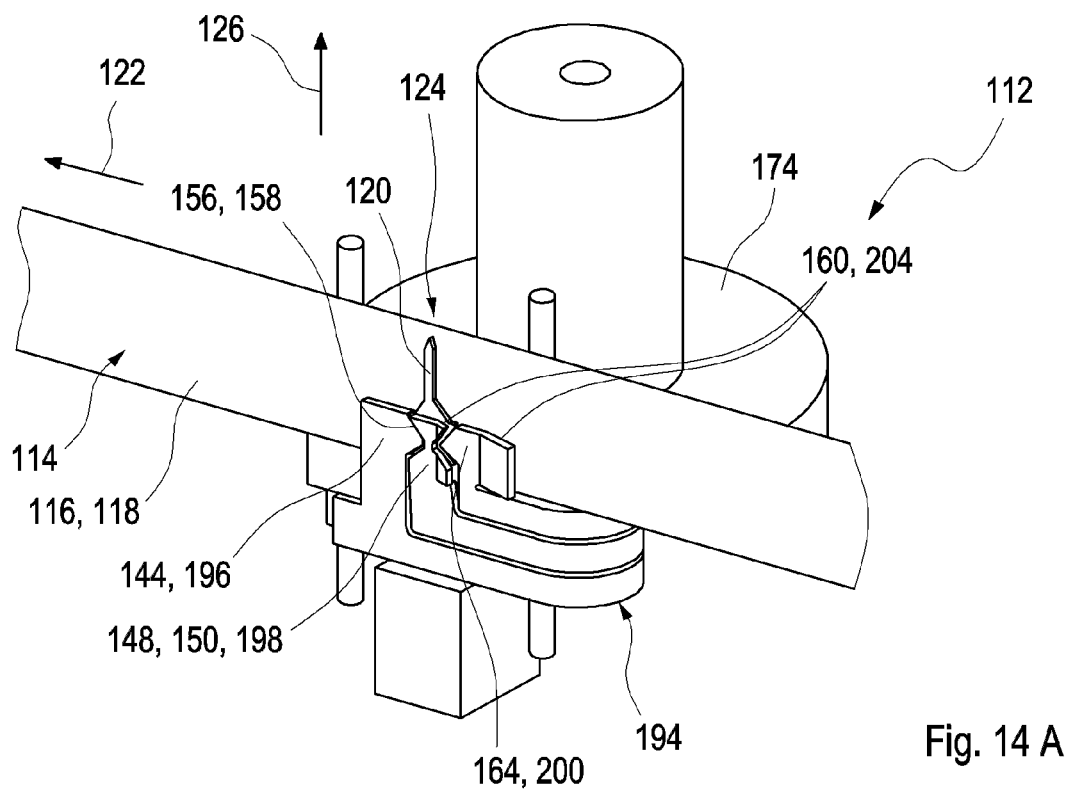
Figure 14:
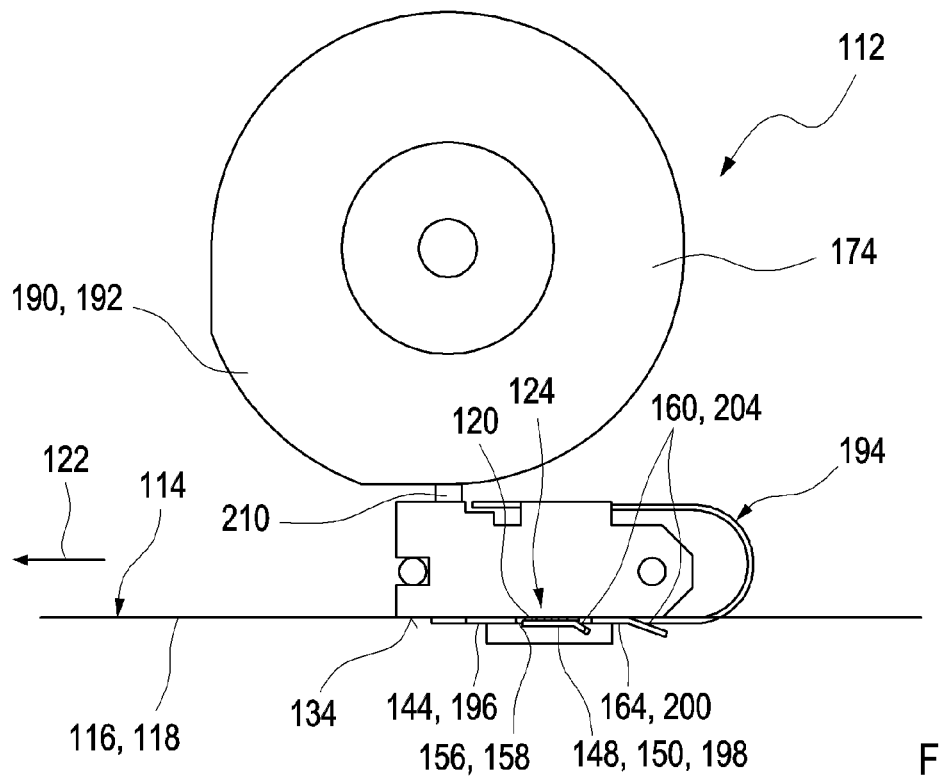
Figure 15:
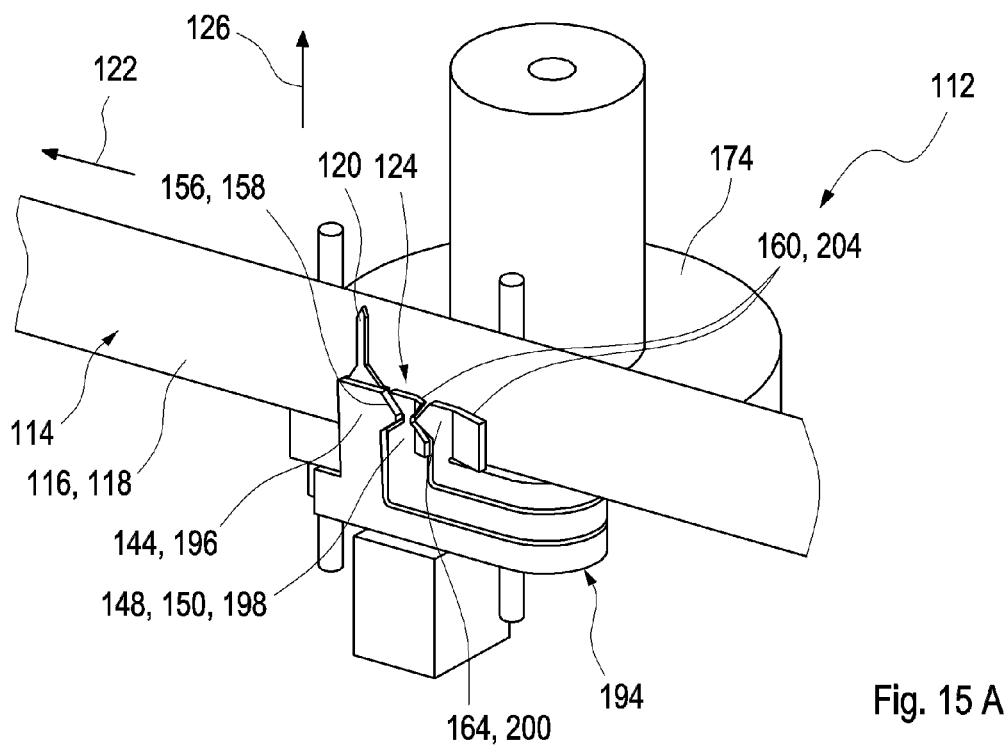
Figure 15:
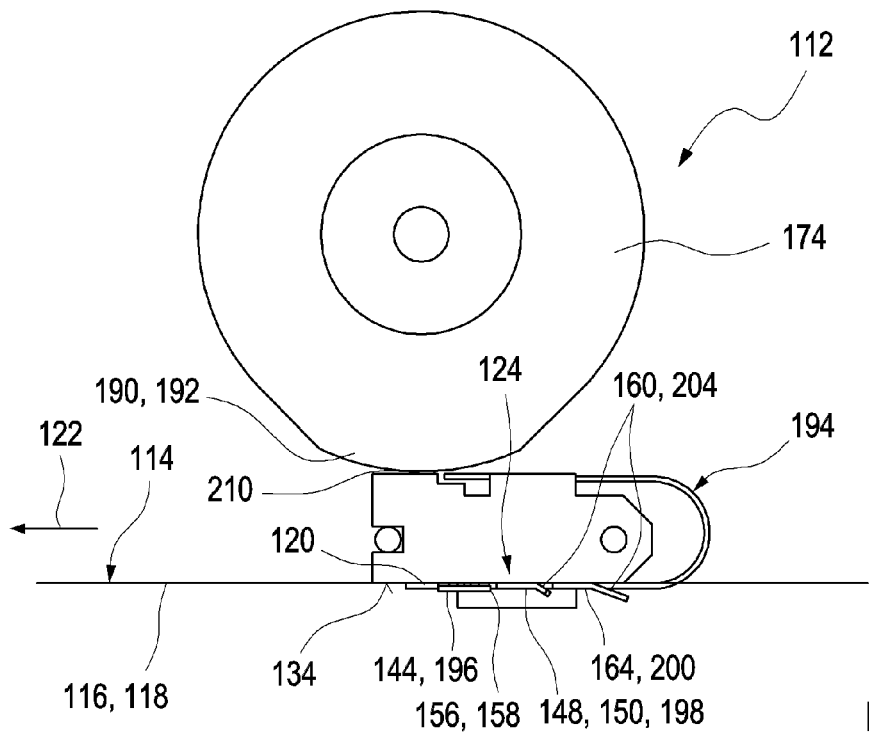
Figure 16:
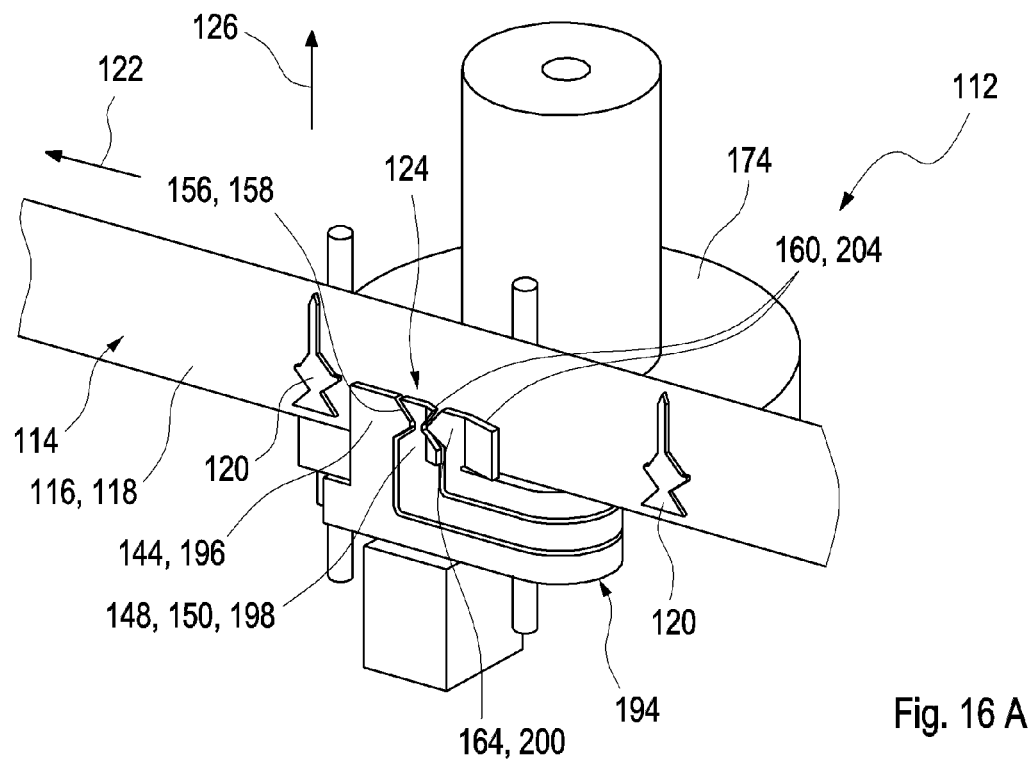
Figure 16:
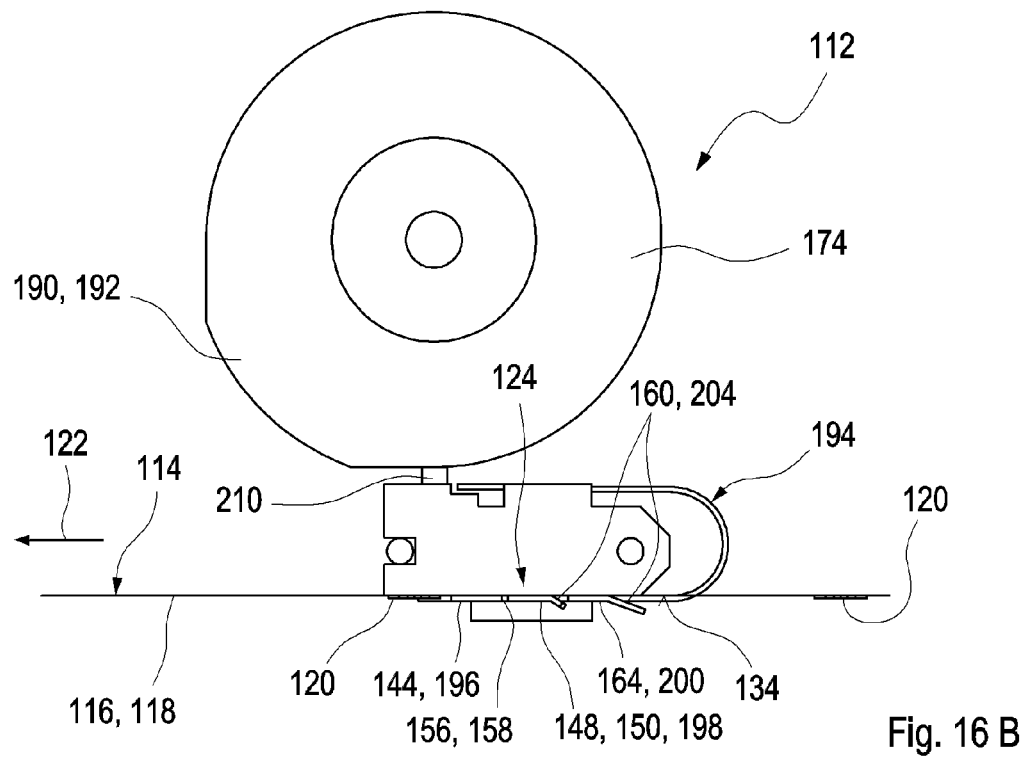

The gripper plate 194 shown in FIG. 4 serves only as an example. Thus, FIG. 6 shows an alternative design of the gripper plate 194, in which this gripper plate 194 is bent in a U-shape. Otherwise, the function of the gripper plate 194 corresponds substantially to the function described above with reference to FIG. 4.

The function of the illustrative embodiments in FIGS. 4 and 6, in each of which gripper plates 194 are used, will briefly be explained on the basis of function sequences set out below. Here, FIGS. 7A to 11B show a function sequence of the illustrative embodiment according to FIG. 4, whereas FIGS. 12A to 16B show a function sequence of the illustrative embodiment according to FIG. 6. In the drawings, the figures designated by "A" each show a perspective view, whereas the corresponding figures designated by "B" show a front view of the gripper device 112 or of parts thereof, with the drawing plane perpendicular to the piercing plane. For the description of the individual elements, reference can largely be made to FIGS. 4 and 6 above.

In the illustrative embodiment in FIGS. 7A to 11B, the piercing direction 126 is perpendicular to the reel axis of the supply reel and/or of the take-up reel and perpendicular to an axis of the driving disk 174. Of this driving disk 174, only the tensioning disk 178 is shown, the gripper driving disk 176 having been omitted for reasons of clarity.

FIGS. 7A and 7B show a situation in which a lancet 120 arrives in front of the gripper device 112. The front view according to FIG. 7B clearly shows the ramp 160 with which, during insertion, the third tongue 200 acting as counter-gripper 164 is opened.

This opening procedure is shown in FIGS. 8A and 8B. In this situation, the lancet 120 passes the counter-gripper 164 and in so doing lifts the third tongue 200. To make it easier to lift the second tongue 198 during this insertion, it is alternatively or additionally possible in this illustrative embodiment, and also in other illustrative embodiments, for the positioning element 148, in particular the holding-down mechanism 150, to have a corresponding ramp 160, which may take the form of an upwardly bent tab 204.

FIGS. 9A and 9B show, finally, a situation in which the lancet 120 has arrived in the application position 124. The lancet 120 is stopped on the abutment edge 158 of the stop element 144 and is thus trapped in the gripper structure. By virtue of its own spring force, the third tongue 200 has moved back down again toward the support surface 134 or the carrier tape 118 of the lancet tape 114. The lancet 120 can move only minimally in this form fit between the stop element 144 and the counter-gripper 164.

The piercing procedure is then carried out in the manner that has been described above. Finally, FIGS. 10A and 10B show a situation in which, after the piercing procedure, the lancet tape 114 is advanced incrementally. By means of the continuation 186, acting as opener, and by means of the ramp 190 or step 192 in the tensioning disk 178, the first tongue 196, that is to say the stop element 144, is lifted, while the lancet 120 can be held by the holding-down mechanism 150. Accordingly, the lancet 120 can be withdrawn from the gripper device 112.

As is shown in FIGS. 11A and 11B, the used lancet 120 is now freed from the gripper device 112, and a lancet 120, which is preferably unused, can be transported into the gripper device 112. In this situation, the first tongue 196, acting as stop tab, once again lies on the carrier tape 118.

FIGS. 12A to 16B show a movement sequence that corresponds to FIGS. 7A to 11B and that pertains to the illustrative embodiment of the gripper device 112 with the gripper plate 194 according to FIG. 6. The piercing direction is in this case along a reel axis of a supply reel and/or of a take-up reel and/or of the driving disk 174. As has been described with reference to FIG. 6, in this illustrative embodiment the first tongue 196 of the gripper plate 194 acts as stop element 144, the second tongue 198 acts as positioning element 148 and holding down-mechanism 150, and the third tongue 200 acts as counter-gripper 164. The driving disk 174 can again have a ramp 190 and/or a step 192 which can, for example, by way of a transfer element 210, act on the first tongue 196 in order to lift the latter.

FIGS. 12A and 12B once again show a situation, analogous to FIGS. 7A and 7B, before a lancet 120 reaches the gripper device 112. FIGS. 13A and 13B show a situation corresponding to the situation in FIGS. 8A and 8B. The lancet 120 has reached the ramp 160 of the third tongue 200 and lifts the latter, so as to move into the gripper device 112.

FIGS. 14A and 14B show a situation, analogous to the situation in FIGS. 9A and 9B, in which the lancet 120 has arrived in the gap 168 next to the first tongue 196 and is stopped by the stop element 144 in the form of the first tongue 196. In this situation, the holding-down mechanism in the form of the second tongue 198 is lifted and presses the lancet 120 downward toward a support surface 134.

FIGS. 15A and 15B show a situation, corresponding to FIGS. 11A and 11B, after a piercing procedure. The first tongue 196, acting as stop element 144, is lifted by the ramp 190 or step 192 of the driving disk 174 via the transfer element 210 (no longer discernible in FIGS. 15A and 15B), such that the lancet 120 can be freed from the gripper device 112. During this procedure, the lancet 120 can be at least partially held by the holding-down mechanism 150, such that the lancet 120, separated from the first tongue, can be pulled out of the gripper device 112.

Finally, FIGS. 16A and 16B show a situation analogous to the situation in FIGS. 11A and 11B. A used lancet 120 is now freed from the gripper device 112, and a new lancet 120 can be transported into the gripper device 112. The first tongue 196, acting as stop tab and stop element 144, is once again active in this situation.

LIST OF REFERENCE NUMERALS

| | |
|---|---|
| 110 | lancet device |
| 112 | gripper device |
| 114 | lancet tape |
| 116 | carrier element |
| 118 | carrier tape |
| 120 | lancet |
| 122 | spooling direction |
| 124 | application position |
| 126 | piercing direction |
| 128 | guide rollers |
| 130 | longitudinal direction |
| 132 | tape deflection |
| 134 | support surface |
| 136 | gripper underpart |
| 138 | guide groove |
| 140 | carrier plate |
| 142 | gripper guide |
| 144 | stop element |
| 146 | seat |
| 148 | positioning element |
| 150 | holding-down mechanism |
| 152 | gripper spring |
| 154 | gripper spring |
| 156 | abutment |
| 158 | abutment edge |
| 160 | ramp |
| 162 | force |
| 164 | counter-gripper |
| 166 | edge |
| 168 | gap |
| 170 | holding area |
| 172 | pierce drive |
| 174 | driving disk |

LIST OF REFERENCE NUMERALS -continued

| | |
|---|---|
| 176 | gripper driving disk |
| 178 | tensioning disk |
| 180 | pierce spring |
| 182 | toothed wheel |
| 184 | trigger mechanism |
| 186 | continuation |
| 188 | ramp |
| 190 | ramp |
| 192 | step |
| 194 | gripper plate |
| 196 | first tongue |
| 198 | second tongue |
| 200 | third tongue |
| 202 | fixing means |
| 204 | tab |
| 206 | lancet tip |
| 208 | constriction |
| 210 | transfer element |

What is claimed is:

1. A gripper device for use in a lancet device for generating a sample of a body fluid, wherein, in the lancet device, a plurality of lancets are provided in succession on a carrier element in an application position, wherein the gripper device is adapted to seize one of the plurality of lancets at a time in the application position and carry out a piercing movement using the one lancet, and wherein the gripper device comprises:
    at least one stop element, wherein the stop element is adapted to stop the one lancet in the application position and temporarily prevent further movement of the carrier element;
    at least one positioning element, wherein the positioning element is adapted to position the one lancet during the piercing movement in at least one direction substantially transverse to a piercing direction; and
    at least one counter-gripper, wherein the counter-gripper is adapted to cooperate with the stop element such that the one lancet is holdable with a form fit.

2. The gripper device of claim 1 wherein the positioning element has at least one holding-down mechanism, wherein the holding-down mechanism is adapted to exert a force on the one lancet perpendicularly with respect to a plane formed by a longitudinal direction of the carrier element and by the piercing direction.

3. The gripper device of claim 1, further comprising a gripper underpart, wherein the gripper device is adapted to guide the carrier element between the gripper underpart and the positioning element and wherein the positioning element is adapted to subject the carrier element to a force in the direction of the gripper underpart.

4. The gripper device of claim 1 wherein the stop element is releasable and, after the piercing procedure has been carried out, is released whereby further movement of the carrier element is again permitted.

5. The gripper device of claim 1 wherein the stop element has at least one abutment wherein the abutment can be positioned adjacent to the carrier element and is configured such that a lancet is stopped on the abutment during a movement of the carrier element and wherein the abutment is movable in a direction transverse to a longitudinal direction of the carrier element to thereby release the stop element.

6. The gripper device of claim 1 wherein at least one of the counter-gripper and the positioning element has at least one ramp wherein the ramp is adapted to allow the lancet to be guided in between the counter-gripper and the stop element.

7. The gripper device of claim 1 further comprising at least one stationary gripper guide, wherein the stop element and the positioning element are mounted movably in the gripper guide.

8. The gripper device of claim 7 wherein the counter-gripper is movably mounted in the gripper guide.

9. The gripper device of claim 1 further comprising at least one gripper spring, wherein the gripper spring is adapted to subject the stop element and the positioning element to a force in the direction of the carrier element.

10. The gripper device of claim 9 wherein the gripper spring is adapted to subject the counter-gripper to a force in the direction of the carrier element.

11. The gripper device of claim 1 wherein the stop element and the positioning element comprise spring components.

12. The gripper device of claim 11 wherein the counter-gripper is designed at least in part as a spring component.

13. The gripper device of claim 11 wherein the stop element and the positioning element comprise tongues of a spring plate, wherein the spring plate has a first tongue acting as the stop element, a second tongue acting as the positioning element.

14. The gripper device of claim 13 wherein the counter-gripper comprises a spring component and the spring plate has a third tongue lying opposite the first tongue and acting as the counter-gripper.

15. A lancet device for generating a sample of a body fluid, wherein, the lancet device is adapted to hold a plurality of lancets provided in succession on a carrier element to an application position, wherein the lancet device comprises:
    a gripper device adapted to seize one of the plurality of lancets at a time in the application position and carry out a piercing movement using the one lancet, wherein the gripper device includes:
    at least one stop element, wherein the stop element is adapted to stop the one lancet in the application position and temporarily prevent further movement of the carrier element;
    at least one positioning element, wherein the positioning element is adapted to position the one lancet during the piercing movement in at least one direction substantially transverse to a piercing direction; and
    at least one counter-gripper, wherein the counter-gripper is adapted to cooperate with the stop element such that the one lancet is holdable with a form fit.

16. The lancet device of claim 15 further comprising at least one pierce drive, wherein the pierce drive is adapted to drive the gripper device to perform the piercing movement, wherein the pierce drive is adapted to release the stop element after the piercing movement and to free the lancet used beforehand for the piercing movement.

17. The lancet device of claim 16 wherein the pierce drive has at least one elevation comprising at least one of a ramp and a step, wherein the elevation is adapted to move at least one abutment of the stop element of the gripper device substantially transversely with respect to a longitudinal direction of the carrier element to thereby release the stop element.

18. The lancet device of claim 16 wherein the pierce drive has at least one driving disk.

19. The lancet device of claim 15 wherein the one lancet has a holding area that can be seized by the gripper device, wherein the holding area has at least one outer contour allowing the one lancet to be subjected to a force parallel to the piercing movement, and wherein the stop element has an inner contour that matches at least approximately the outer contour of the holding area.

20. The lancet device of claim 19 wherein the counter-gripper has an inner contour that matches at least approximately the outer contour of the holding area.

21. The lancet device of claim 15 wherein the positioning element has at least one holding-down mechanism, wherein the holding-down mechanism is adapted to exert a force on the one lancet substantially perpendicularly with respect to a plane formed by a longitudinal direction of the carrier element and by the piercing direction.

22. The lancet device of claim 15 wherein the gripper device further comprises a gripper underpart, wherein the gripper device is adapted to guide the carrier element between the gripper underpart and the positioning element and wherein the positioning element is adapted to subject the carrier element to a force in the direction of the gripper underpart.

23. The lancet device of claim 15 wherein the stop element is releasable and, after the piercing procedure has been carried out, is released whereby further movement of the carrier element is again permitted.

24. The lancet device of claim 15 wherein the stop element has at least one abutment wherein the abutment can be positioned adjacent to the carrier element and is configured such that a lancet is stopped on the abutment during a movement of the carrier element and wherein the abutment is movable in a direction substantially transverse to a longitudinal direction of the carrier element to thereby release the stop element.

25. The lancet device of claim 15 wherein at least one of the counter-gripper and the positioning element has at least one ramp wherein the ramp is adapted to allow the lancet to be guided in between the counter-gripper and the stop element.

26. The lancet device of claim 15 wherein the gripper device further comprises at least one stationary gripper guide, wherein the stop element and the positioning element are mounted movably in the gripper guide.

27. The lancet device of claim 26 wherein the counter-gripper is movably mounted in the gripper guide.

28. The lancet device of claim 15 further comprising at least one gripper spring, wherein the gripper spring is adapted to subject the stop element and the positioning element to a force in the direction of the carrier element.

29. The lancet device of claim 28 wherein the gripper spring is adapted to subject the counter-gripper to a force in the direction of the carrier element.

30. The lancet device of claim 15 wherein the stop element and the positioning element comprise spring components.

31. The lancet device of claim 30 wherein the counter-gripper comprises a spring component.

32. The lancet device of claim 30 wherein the stop element and the positioning element comprise tongues of a spring plate, wherein the spring plate has a first tongue acting as the stop element, a second tongue acting as the positioning element.

33. The lancet device of claim 32 wherein the counter-gripper comprises a spring component and the spring plate has a third tongue lying opposite the first tongue and acting as the counter-gripper.

* * * * *